US009164097B2

(12) United States Patent
Stanimirovic et al.

(10) Patent No.: US 9,164,097 B2
(45) Date of Patent: Oct. 20, 2015

(54) FORMULATIONS TARGETING IGFBP7 FOR DIAGNOSIS AND THERAPY OF CANCER

(75) Inventors: Danica Stanimirovic, Greely (CA); Abedelnasser Abulrob, Orleans (CA); Maria Moreno, Ottawa (CA)

(73) Assignee: National Research Council of Canada, Ottawa (CA)

( * ) Notice: Subject to any disclaimer, the term of this patent is extended or adjusted under 35 U.S.C. 154(b) by 1132 days.

(21) Appl. No.: 13/124,314

(22) PCT Filed: Oct. 14, 2009

(86) PCT No.: PCT/CA2009/001460
§ 371 (c)(1),
(2), (4) Date: Jun. 6, 2011

(87) PCT Pub. No.: WO2010/043037
PCT Pub. Date: Apr. 22, 2010

(65) Prior Publication Data
US 2012/0045391 A1 Feb. 23, 2012

Related U.S. Application Data

(60) Provisional application No. 61/105,212, filed on Oct. 14, 2008.

(51) Int. Cl.
C07K 16/18 (2006.01)
A61K 39/395 (2006.01)
G01N 33/53 (2006.01)
G01N 23/04 (2006.01)
G01N 23/083 (2006.01)
G01N 33/574 (2006.01)
A61K 49/00 (2006.01)
C07K 16/32 (2006.01)
G01N 33/68 (2006.01)
A61K 39/00 (2006.01)

(52) U.S. Cl.
CPC ...... *G01N 33/57407* (2013.01); *A61K 49/0032* (2013.01); *A61K 49/0058* (2013.01); *C07K 16/32* (2013.01); *G01N 33/6854* (2013.01); *A61K 2039/505* (2013.01); *C07K 2317/22* (2013.01); *C07K 2317/569* (2013.01); *G01N 2333/4745* (2013.01)

(58) Field of Classification Search
CPC ...... C07K 16/18; C07K 16/46; C07K 16/464; C07K 16/465; C07K 2317/22; C07K 2317/24; C07K 14/4743; A61K 39/395; G01N 33/5005; G01N 33/5091; G01N 33/53; G01N 33/532; G01N 33/56966; G01N 33/574; G01N 33/74
See application file for complete search history.

(56) References Cited

U.S. PATENT DOCUMENTS 7,858,091 B2 * 12/2010 Yamano et al. ............ 424/145.1

OTHER PUBLICATIONS

Stockwin, L.H., et al., Expert Opin. Biol. Ther., 3(7):1133-1152, 2003.*
Jianbing Zhang et al., "Pentamerization of Single-domain Antibodies from Phage Libraries: A Novel Strategy for the Rapid Generation of High-avidity Antibody Reagents", Journal of Molecular Biology, 2004, 335, pp. 49-56, Elsevier Ltd, UK.
John De Kruif et al., "Leucine Zipper Dimerized Bivalent and Bispecific scFv Antibodies from a Semi-synthetic Antibody Phage Display Library", The Journal of Biological Chemistry, 1996, vol. 271, No. 13, Issue of Mar. 29, pp. 7630-7634, The American Society for Biochemistry and Molecular Biology, Inc., USA.
C. Hamers.Casterman et al., "Naturally occurring antibodies devoid of light chains", Letters to Nature, Jun. 3, 1993, vol. 363 pp. 446-448, Nature Publishing Group, United Kingdom.
Laurent Jaspers et al., "Aggregation-resistant domain antibodies selected on phage by heat denaturation", Nature Biotechnology, Sep. 2004, vol. 22 No. 9, pp. 1161-1165, Nature Publishing Group, UK.
Ulrik B. Nielsen et al., "Targeting of Bivalent Anti-ErbB2 Diabody Antibody Fragments to Tumor Cells Is Independent of the Intrinsic Antibody Affinity", Cancer Research, Nov. 15, 2000, 60, pp. 6434-6440, American Association for Cancer Research, USA.
Stewart D. Nuttall et al., "Isolation and characterization of an IgNAR variable domain specific for the human mitochondrial translocase receptor Tom70", Eur. J. Biochem, 2003, 270, pp. 3543-3554, The Federation of the European Biochemical Societies, UK.
Eduardo A. Padlan, "Anatomy of the Antibody Molecule", Molecular Immunology, 1994, vol. 31, No. 3, pp. 169-217, Elsevier Science Ltd., UK.
John B.B.Ridgway et al., "'Knobs-into-holes' engineering of antibody CH3 domains for heavy chain heterodimerization", Protein Engineering, 1996, vol. 9 No. 7 pp. 617-621, Oxford University Press, UK.
Jianbing Zhang et al., "A Pentavalent Single-domain Antibody Approach to Tumor Antigen Discovery and the Development of Novel Proteomics Reagents", Journal of Molecular Biology, 2004, 341, pp. 161-169, Elsevier Ltd, UK.
Rebecca To et al., "Isolation of Monomeric Human $V_HS$ by a Phage Selection", The Journal of Biological Chemistry, Dec. 16, 2005, vol. 280, No. 50, pp. 41395-41403, The American Society for Biochemistry and Molecular Biology, Inc., USA.

* cited by examiner

Primary Examiner — Misook Yu
Assistant Examiner — Anne Holleran
(74) Attorney, Agent, or Firm — Frommer Lawrence & Haug LLP

(57) ABSTRACT

The invention relates to antibodies or fragments thereof specific for insulin-like growth factor binding protein-7 (IGFBP7). A method of raising anti-IGFBP7 single domain antibodies is also disclosed and specific antibody clones are described, along with their binding characteristics. The anti-IGFBP7 antibodies may be useful as diagnostic tools for detecting neoplastic diseases involving tumor angiogenesis, and a variety of other angiogenesis associated diseases.

21 Claims, 31 Drawing Sheets

Figure 1.

- SEQ ID NO. 1 (Clone 4.6-I)
  AIAIAVALAGFATVAQAQVKLEESGGGSVQPGGSLRLSCA
  ASGRTFSRLAMGWFRQAPGKERELVAGISRSGDGTHYAY
  SVKGRFTISRDNAANTVELQMNSLKPEDTAVYFCAAARTA
  FYYYGNDYNYWGQGTQVTVSS

- SEQ ID NO. 2 (Clone 4.43-I)
  AIAIAVALAGFATVAQAQVKLEESGGGLVQAGGSLRLSCA
  ASGRTSRRYAMGWFRQAPGKEREFVAGISRSGDGTHYA
  YSVKGRFTISRDNAANTVELQMNSLKPEDTAVYFCAAART
  AFYYYGNDYNYWGQGTQVTVSS

Figure 9.
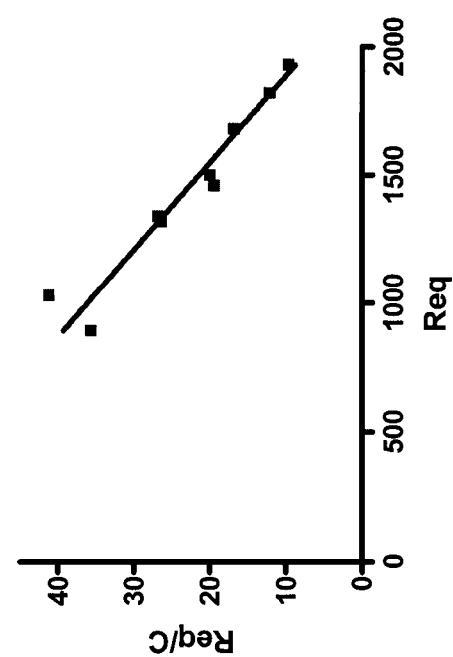
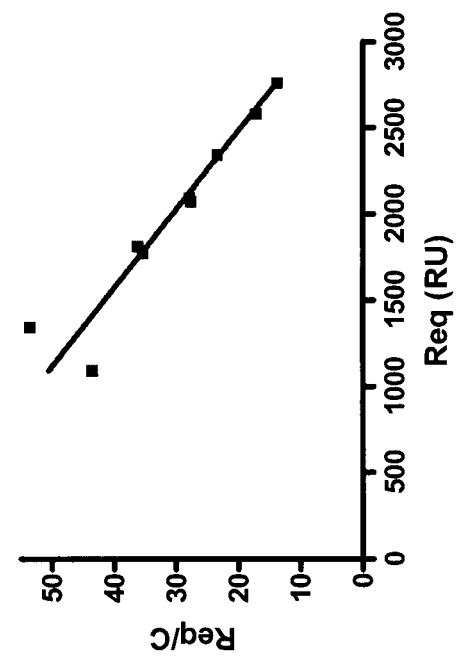

Figure 14. Schematic drawing of clone 4.43-IGFBP7 conjugation to Cy5.5

Clone 4.43-IGFBP7-Cy5.5 conjugate (25 microgram) injected i.v.

NC11 sdAb (negative control) -Cy5.5 conjugate (25 microgram) injected i.v.

Schematic drawing of pentameric clone 4.43-IGFBP7 + conjugation to Cy5.5

Clone 4.43-IGFBP7-Cy5.5-pentamer injected i.v.

Accumulation of Clone 4.43-IGFBP7-Cy5.5-pentamer in the head after i.v. injection

Figure 24.
Clone 4.43-IGFBP7-Cy5.5-pentamer injected i.v.
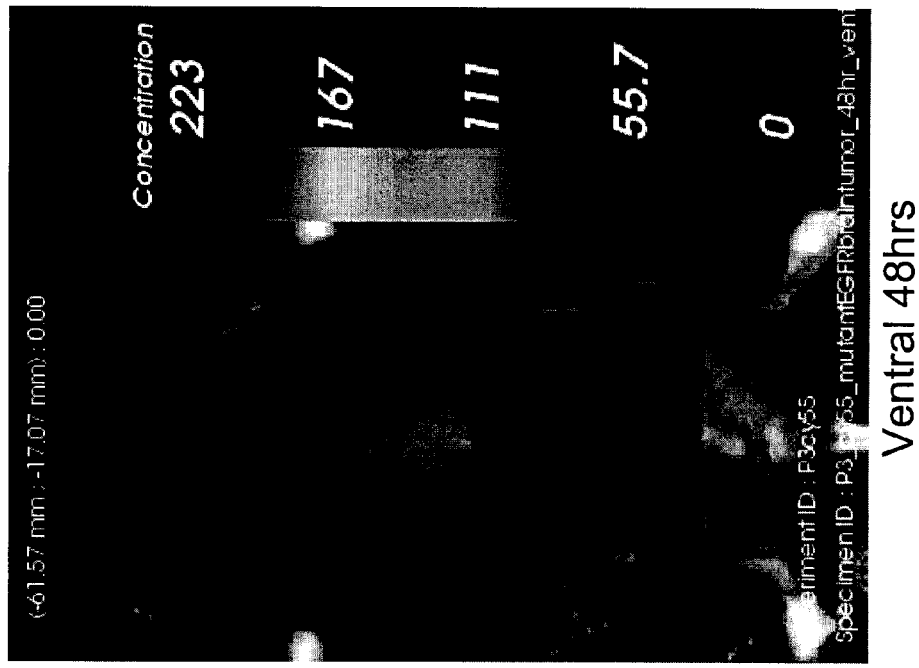
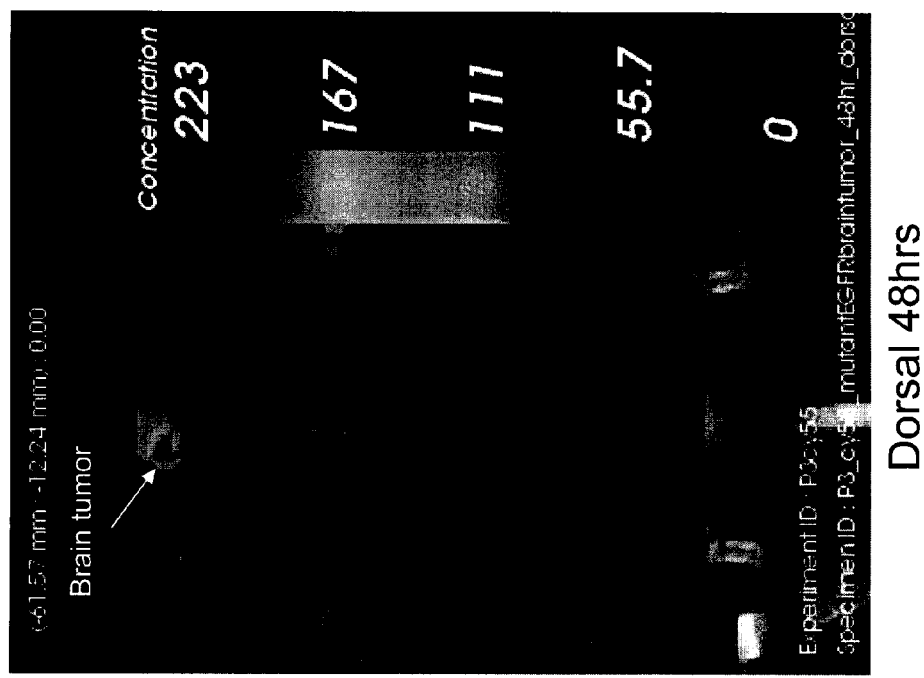
Dorsal 48hrs
Ventral 48hrs Clone 4.43-IGFBP7-Cy5.5-pentamer Biodistribution of Clone 4.43-IGFBP7-Cy5.5-pentamer 48h post-injection

|  | Total Fluorescence Concentration | Average Fluorescence Concentration |
|---|---|---|
| Brain | 129 | 12.9 |
| heart | 1.63 | 0.407 |
| kidney | 31.8 | 2.12 |
| lung | 18.3 | 2.03 |
| liver | 120 | 4.45 |
| spleen | 0.46 | 0.154 |
| muscle | 2.82 | 0.939 |

Figure 29. Anti-IGFBP7 sdAb after 24 hours in normal brain

Effect of 4.43 IGFBP7 sdAb on Angiogenesis of HCEC (Matrigel assay)

SEQUENCE LISTING

```
<160> NUMBER OF SEQ ID NOS: 16

<210> SEQ ID NO 1
<211> LENGTH: 140
<212> TYPE: PRT
<213> ORGANISM: Artificial Sequence
<220> FEATURE:
<223> OTHER INFORMATION: anti-IGFBP7 clone 4.6

<400> SEQUENCE: 1

Ala Ile Ala Ile Ala Val Ala Leu Ala Gly Phe Ala Thr Val Ala Gln
```

```
            1               5              10              15
        Ala Gln Val Lys Leu Glu Glu Ser Gly Gly Gly Ser Val Gln Pro Gly
                        20              25              30

Gly Ser Leu Arg Leu Ser Cys Ala Ala Ser Gly Arg Thr Phe Ser Arg
                        35              40              45

Leu Ala Met Gly Trp Phe Arg Gln Ala Pro Gly Lys Glu Arg Glu Leu
                50              55              60

Val Ala Gly Ile Ser Arg Ser Gly Asp Gly Thr His Tyr Ala Tyr Ser
         65              70              75              80

Val Lys Gly Arg Phe Thr Ile Ser Arg Asp Asn Ala Ala Asn Thr Val
                        85              90              95

Glu Leu Gln Met Asn Ser Leu Lys Pro Glu Asp Thr Ala Val Tyr Phe
                       100             105             110

Cys Ala Ala Arg Thr Ala Phe Tyr Tyr Gly Asn Asp Tyr Asn
                       115             120             125

Tyr Trp Gly Gln Gly Thr Gln Val Thr Val Ser Ser
               130             135             140

<210> SEQ ID NO 2
<211> LENGTH: 140
<212> TYPE: PRT
<213> ORGANISM: Artificial Sequence
<220> FEATURE:
<223> OTHER INFORMATION: anti-IGFBP7 clone 4.43

<400> SEQUENCE: 2

Ala Ile Ala Ile Ala Val Ala Leu Ala Gly Phe Ala Thr Val Ala Gln
         1               5              10              15

Ala Gln Val Lys Leu Glu Glu Ser Gly Gly Gly Leu Val Gln Ala Gly
                        20              25              30

Gly Ser Leu Arg Leu Ser Cys Ala Ala Ser Gly Arg Thr Ser Arg Arg
                        35              40              45

Tyr Ala Met Gly Trp Phe Arg Gln Ala Pro Gly Lys Glu Arg Glu Phe
                50              55              60

Val Ala Gly Ile Ser Arg Ser Gly Asp Gly Thr His Tyr Ala Tyr Ser
         65              70              75              80

Val Lys Gly Arg Phe Thr Ile Ser Arg Asp Asn Ala Ala Asn Thr Val
                        85              90              95

Glu Leu Gln Met Asn Ser Leu Lys Pro Glu Asp Thr Ala Val Tyr Phe
                       100             105             110

Cys Ala Ala Arg Thr Ala Phe Tyr Tyr Gly Asn Asp Tyr Asn
                       115             120             125

Tyr Trp Gly Gln Gly Thr Gln Val Thr Val Ser Ser
               130             135             140

<210> SEQ ID NO 3
<211> LENGTH: 8
<212> TYPE: PRT
<213> ORGANISM: Artificial Sequence
<220> FEATURE:
<223> OTHER INFORMATION: CDR2 of clone 4.6

<400> SEQUENCE: 3

Arg Thr Phe Ser Arg Leu Ala Met
         1               5

<210> SEQ ID NO 4
<211> LENGTH: 15
```

```
<212> TYPE: PRT
<213> ORGANISM: Artificial Sequence
<220> FEATURE:
<223> OTHER INFORMATION: CDR2 of clones 4.43 and 4.6

<400> SEQUENCE: 4

Gly Ile Ser Arg Ser Gly Asp Gly Thr His Tyr Ala Tyr Ser Val
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: CDR2 of clone 4.6

<400> SEQUENCE: 5

Ala Ala Arg Thr Ala Phe Tyr Tyr Tyr Gly Asn Asp Tyr Asn Tyr
1               5                   10                  15

<210> SEQ ID NO 6
<211> LENGTH: 8
<212> TYPE: PRT
<213> ORGANISM: Artificial Sequence
<220> FEATURE:
<223> OTHER INFORMATION: CDR2 of clone 4.43

<400> SEQUENCE: 6

Arg Thr Ser Arg Arg Tyr Ala Met
1               5

<210> SEQ ID NO 7
<211> LENGTH: 16
<212> TYPE: PRT
<213> ORGANISM: Artificial Sequence
<220> FEATURE:
<223> OTHER INFORMATION: CDR2 of clone 4.43

<400> SEQUENCE: 7

Ala Ala Ala Arg Thr Ala Phe Tyr Tyr Tyr Gly Asn Asp Tyr Asn Tyr
1               5                   10                  15

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
tcgaattccc gccatggagc ggccgtcg                                    28

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
tagggatcct agctcggcac cttcacct                                    28

<210> SEQ ID NO 10
<211> LENGTH: 45
<212> TYPE: DNA
<213> ORGANISM: Artificial Sequence
<220> FEATURE:
```

<223> OTHER INFORMATION: Primer MJ1

<400> SEQUENCE: 10
gcccagccgg ccatggccsm kgtgcagctg gtggaktctg gggga                45

<210> SEQ ID NO 11
<211> LENGTH: 42
<212> TYPE: DNA
<213> ORGANISM: Artificial Sequence
<220> FEATURE:
<223> OTHER INFORMATION: Primer MJ2

<400> SEQUENCE: 11
cagccggcca tggcccaggt aaagctggag gagtctgggg ga                   42

<210> SEQ ID NO 12
<211> LENGTH: 45
<212> TYPE: DNA
<213> ORGANISM: Artificial Sequence
<220> FEATURE:
<223> OTHER INFORMATION: Primer MJ3

<400> SEQUENCE: 12
gcccagccgg ccatggccca ggctcaggta cagctggtgg agtct                45

<210> SEQ ID NO 13
<211> LENGTH: 21
<212> TYPE: DNA
<213> ORGANISM: Artificial Sequence
<220> FEATURE:
<223> OTHER INFORMATION: Primer CH2

<400> SEQUENCE: 13
cgccatcaag gtaccagttg a                                          21

<210> SEQ ID NO 14
<211> LENGTH: 29
<212> TYPE: DNA
<213> ORGANISM: Artificial Sequence
<220> FEATURE:
<223> OTHER INFORMATION: Primer CH2b3

<400> SEQUENCE: 14
ggggtacctg tcatccacgg accagctga                                  29

<210> SEQ ID NO 15
<211> LENGTH: 34
<212> TYPE: DNA
<213> ORGANISM: Artificial Sequence
<220> FEATURE:
<223> OTHER INFORMATION: Primer MJ7BACK

<400> SEQUENCE: 15
catgtgtaga ctcgcggccc agccggccat ggcc                            34

<210> SEQ ID NO 16
<211> LENGTH: 47
<212> TYPE: DNA
<213> ORGANISM: Artificial Sequence
<220> FEATURE:
<223> OTHER INFORMATION: Primer MJ8FOR

<400> SEQUENCE: 16
catgtgtaga ttcctggccg gcctggcctg aggagacggt gacctgg              47

FORMULATIONS TARGETING IGFBP7 FOR DIAGNOSIS AND THERAPY OF CANCER

This application is a 371 of PCT/CA 2009/001460 filed on Oct. 14, 2009 published on Apr. 22, 2010 under publication number WO 2010/043037 A which claims priority benefits to U.S. Provisional Patent Application Ser. No. 61/105,212 filed Oct. 14, 2008, the disclosure of which is incorporated herein by reference.

FIELD OF THE INVENTION

The present invention relates to isolation of single domain antibodies against Insulin-like Growth Factor Binding Protein 7 (IGFBP7) that specifically target glioblastoma tumor vessels, and to their use as diagnostic tools for detecting neoplastic diseases and as therapeutic agents for reducing tumor angiogenesis.

BACKGROUND OF THE INVENTION

Malignant brain tumors, glioblastoma multiforme (GBM), are a fatal form of cancer. Despite advances in neurosurgical techniques, chemotherapeutic regimens, and radiotherapy protocols, the median survival following surgical resection and adjuvant therapy is less than 12 months. Glioblastomas have one of the highest rates of angiogenesis among all malignant tumors. The level of angiogenesis in glioblastomas is a direct predictor of patient survival.

However, non-invasive diagnostic/prognostic assessment of the angiogenesis in glioblastomas by imaging techniques is lacking. Similarly, there are no effective anti-angiogenic therapies for glioblastomas. Developing imaging, diagnostic and therapeutic approaches to assess and inhibit angiogenesis in glioblastomas, respectively, depends on the characterization of specific markers of brain tumor angiogenesis that could serve as targets.

Typically, GBM is diagnosed as an area of contrast enhancement on MRI—this technique does not provide useful information on the molecular characteristics of GBM nor about the rate of angiogenesis.

GBM therapy currently includes neurosurgical tumor removal followed by highly toxic radio- and chemo-therapeutic regimens (and several experimental treatments). However the success rate remains low.

The key reason for failure of neurosurgical intervention in curing GBM is cancer recurrence. Recurrence occurs because of the locally invasive nature of the tumor—microscopic regional metastases are not removed during surgery and cause tumor recidive. Failure of chemotherapeutic treatments is due to poor penetration of drugs across the blood-tumor barrier.

Accordingly, it is desirable to develop diagnostic and/or therapeutic formulations that specifically recognize abnormal blood vessels in brain tumors. These formulations could be adapted for use in molecular imaging (optical, MRI, PET) in vivo to diagnose brain tumor and evaluate the extent of angiogenesis and invasion, to prevent growth of abnormal tumor vessels, and/or to target/deliver other therapeutics to tumor vessels to destroy tumor vessels.

SUMMARY OF THE INVENTION

The present invention relates to isolation of single domain antibodies against IGFBP7 that specifically target glioblastoma tumor vessels, and to their use as diagnostic tools for detecting neoplastic diseases and as therapeutic agents for reducing tumor angiogenesis.

The present invention provides an isolated or purified antibody or fragment thereof, comprising
    the sequence of complementarity determining region (CDR) 1 selected from sequences comprising RTFSRLAM (SEQ ID NO:3) and RTSRRYAM (SEQ ID NO:6);
    the sequence of CDR2 comprising GISRSGDGTHYAYSV (SEQ ID NO:4); and
    the sequence of CDR3 selected from sequences comprising AARTAFYYYGNDYNY (SEQ ID NO:5) and AAARTAFYYYGNDYNY (SEQ ID NO:7),
wherein the antibody or fragment thereof binds to Insulin-like Growth Factor Binding Protein 7 (IGFBP7).

The isolated or purified antibody or fragment thereof may be a single-domain antibody (sdAb); the sdAb may be of camelid origin.

The isolated or purified antibody or fragment thereof of the present invention may comprise the sequence:
AIAIAVALAGFATVAQAQVKLEESGGGS-VQPGGSLRLSCAASGRTFSRLAMGWFRQ APGK-ERELVAGISRSGDGTHYAYSVKGRFTIS-RDNAANTVELQMNSLKPEDTAVYFC AAARTAFYYYGNDYNYWGQGTQVTVSS (SEQ ID NO:1), or a sequence substantially identical thereto, or
AIAIAVALAGFATVA-QAQVKLEESGGGLVQAGGSLRLSCAAS-GRTSRRYAMGWFRQ APGKEREFVAGISRSGDGTH-YAYSVKGRFTISRDNAANTVELQMNSLKPEDTAVY FC AAARTAFYYYGNDYNYWGQGTQVTVSS (SEQ ID NO. 2), or a sequence substantially identical thereto.

The present invention also provides an isolated or purified antibody or fragment thereof as described above, wherein the antibody or fragment thereof is in a multivalent display.

The present invention further provides a nucleic acid molecule and/or a vector encoding the isolated or purified antibody or fragment thereof as described herein.

The present invention also provides an isolated or purified antibody or fragment thereof as described above, further comprising a detectable marker. The detectable marker may be selected from the group consisting of radioisotopes, fluorochromes, dyes, enzymes and biotin.

The present invention also encompasses humanized antibody fragments wherein one or more than one of the complementary-determining regions defined herein are grafted to a human variable region ($V_H$H or $V_L$), and wherein the conformation of said one or more than one complementary-determining region is preserved, and the affinity and specificity of the sdAb for its target (i.e., IGFBP7) is also preserved.

The antibodies or fragments of the present invention may be conjugated to a member of the group consisting of cytotoxic agents, cytostatic drugs and glycoproteins.

Also provided is a method for detecting IGFBP7 in a biological sample, comprising the steps of:
a) exposing a sample suspected of containing IGFBP7 to a detectably labelled anti-IGFBP7 antibody;
b) washing the sample; and
c) detecting the presence of said detectably labelled anti-IGFBP7 antibody in said sample.

The biological sample is a solution comprising blood cells, tissue cells, or a solid tissue specimen. The cells in the sample may be selected from the group consisting of brain, lung, colon, pancreas, stomach, and breast tissue specimens.

The present invention also provides a method for diagnosing diseases characterized by proliferation of endothelial cells, comprising the steps of:

a) obtaining a tissue sample from a patient suspected of having a disease characterized by proliferation of endothelial cells;
b) exposing said tissue sample to a detachably labelled anti-IGFBP7 antibody;
c) washing said tissue sample; and
d) detecting the presence of said detectably labelled anti-IGFBP7 antibody in said tissue sample.

The disease may be selected from the group consisting of neoplastic diseases, such as brain cancer, or diseases involving tumor angiogenesis. Alternatively, the disease may be selected from the group consisting of Grade I, II, III, and IV brain gliomas.

The present invention further provides a method for imaging neovascularization in an organism, comprising the steps of:
a) administering to said organism a detectably labelled anti-IGFBP7 antibody into circulation; and
b) detecting an amount of said detectably labelled anti-IGFBP7 antibody which binds to said site.

Also provided is an in vivo method for predicting brain tumor growth by detecting or evaluating neovascularization of brain blood vessel of a subject comprising:
a) administering to the subject an effective amount of anti-IGFB7 antibody contrast agent;
b) detecting said agent thereby forming an image of said accumulated anti-IGFBP7 in said vessel; and
c) predicting risk of brain tumor in the subject based on the image formed.

In the method as just described, the step of predicting may be made based on a quantitative measure of the accumulation of the contrast agent in the brain tumor vessel of the subject.

Additionally, in the methods described above, the step of detecting may be a method selected from the group consisting of x-ray imaging, computed tomography (CT), optical imaging, computed tomography angiography (CTA), electron beam (EBT), magnetic resonance imaging (MRI), magnetic resonance angiography (MRA), and positron emission tomography, gamma camera or with SPECT.

The present invention also provides a method of inhibiting angiogenesis in brain endothelial cells associated with cancer cells, comprising binding the antibody or fragment thereof of the present invention to IGFBP7.

Compositions are also provided by the present invention. Such compositions may comprise the antibody or fragment thereof of as described herein and a pharmaceutically acceptable excipient or carrier. The composition may be used in a method for alleviating the symptoms of a disease characterized by abnormal growth of endothelial cells, where the composition is administered to a patient suspected of having a disease characterized by abnormal growth of endothelial cells.

According to one aspect of the invention, single domain antibodies against IGFBP7 that specifically target glioblastoma tumor vessels were isolated and novel antibodies which are reactive with insulin-like growth factor binding protein-7 (IGFBP7), a cell-adhesive glycoprotein found in endothelial cells and in certain tumor cell populations are described. The method of raising anti-IGFBP7 single domain antibodies is described and the antibody clones 4.6 and 4.43 are provided. Binding characteristics of these clones to IGFBP7 are described.

Anti-IGFBP7 single domain antibodies are useful as diagnostic tools for detecting neoplastic diseases involving tumor angiogenesis, and a variety of other angiogenesis associated diseases. It is therefore an object of the present invention to provide diagnostic methods for detecting angiogenic brain endothelial cells in brain tissue samples. The detection of angiogenic vessels using anti-IGFBP7 single domain antibodies in sections of human brain tumors (removed by surgical intervention), and in sections of experimental glioblastoma tumors (from animals injected orthotopically with U87MG glioblastoma cells) is described.

It is also an object of this invention to provide diagnostic method for detecting and localizing brain tumors in animals and humans using anti-IGFBP7 single domain antibody detectably labeled with contrast agent for optical, MRI, PET or other imaging modalities and injected into circulatory system.

It also an object of this invention to provide therapeutic methods for reducing growth of tumors by inhibiting angiogenesis using anti-IGFBP7 antibody injected into circulatory system or anti-IGFBP7 antibody chemically linked to cytotoxic drugs.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

The invention will now be described in more detail with reference to the accompanying drawings, in which:

FIG. 1 shows amino acid sequences of single-domain antibodies against IGFBP7, in accordance with the present invention. Complementarity-determining region (CDR) 1, 2, and 3 are shown in bold lettering.

FIG. 7A is a steady state affinity analysis, with sensorgram overlays showing the binding of 4.43-IGFBP7 to immobilized recombinant IGFBP7 (left panel) or custom-synthesized recombinant IGFBP7 (right panel), at concentrations of 25, 25, 50, 50, 75, 75, 100, 150, and 200 nM sdAb. FIG. 7B is a sensorgram showing the binding of 100 nM IGFBP7-4.43 to immobilized IGFBP7-4.43 at a surface density of 800 RUs.

FIG. 9 shows the steady state analysis of anti-IGFBP7-4.43 monomer as a Scatchard Plot. Anti-IGFBP7-4.43 was used at concentrations of 25, 25, 50, 50, 75, 75, 100, 150, and 200 nM. FIG. 9A shows results where the ligand is recombinant protein IGFBP7 from R&D ($K_D$ (M): $5 \times 10^{-8}$). FIG. 9B shows results using recombinant custom-synthesized IGFBP7 ($K_D$ (M): $3 \times 10^{-8}$).

FIG. 24 shows a whole body (dorsal and ventral) imaging scan of mice bearing orthotopic brain tumor, 48 h after i.v. injection of pentameric 4.43 IGFBP7-Cy5.5.

DETAILED DESCRIPTION OF THE PREFERRED EMBODIMENTS

Figure 2:
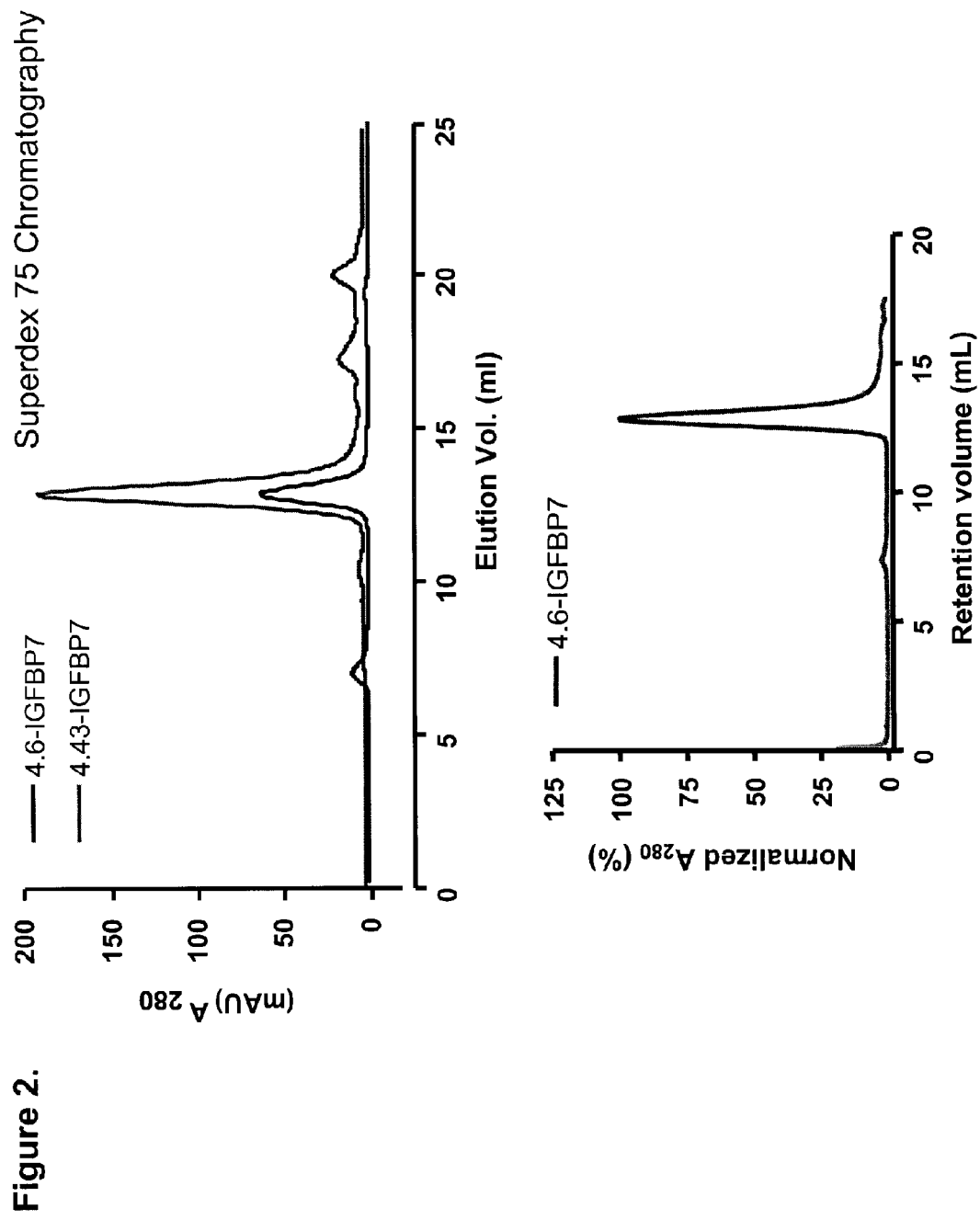
FIG. 2 shows the size-exclusion chromatography of sdAb clones 4.6-IGFBP7 and 4.43-IGFBP7. After being expressed and purified, both clones were shown to be monomeric.
Figure 3:
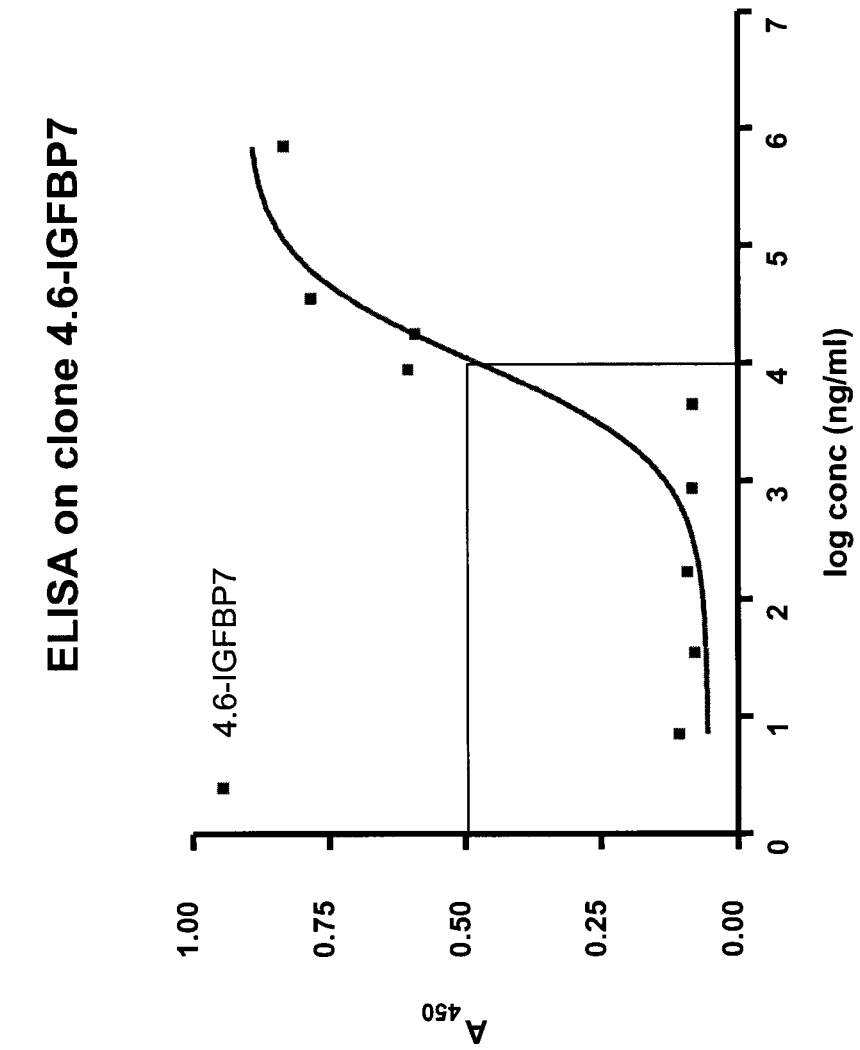
FIG. 3 shows a standard ELISA in which IGFBP7 was coated on microtitre plates and binding of sdAb clone 4.6-IGFBP7 was assessed.
Figure 4:
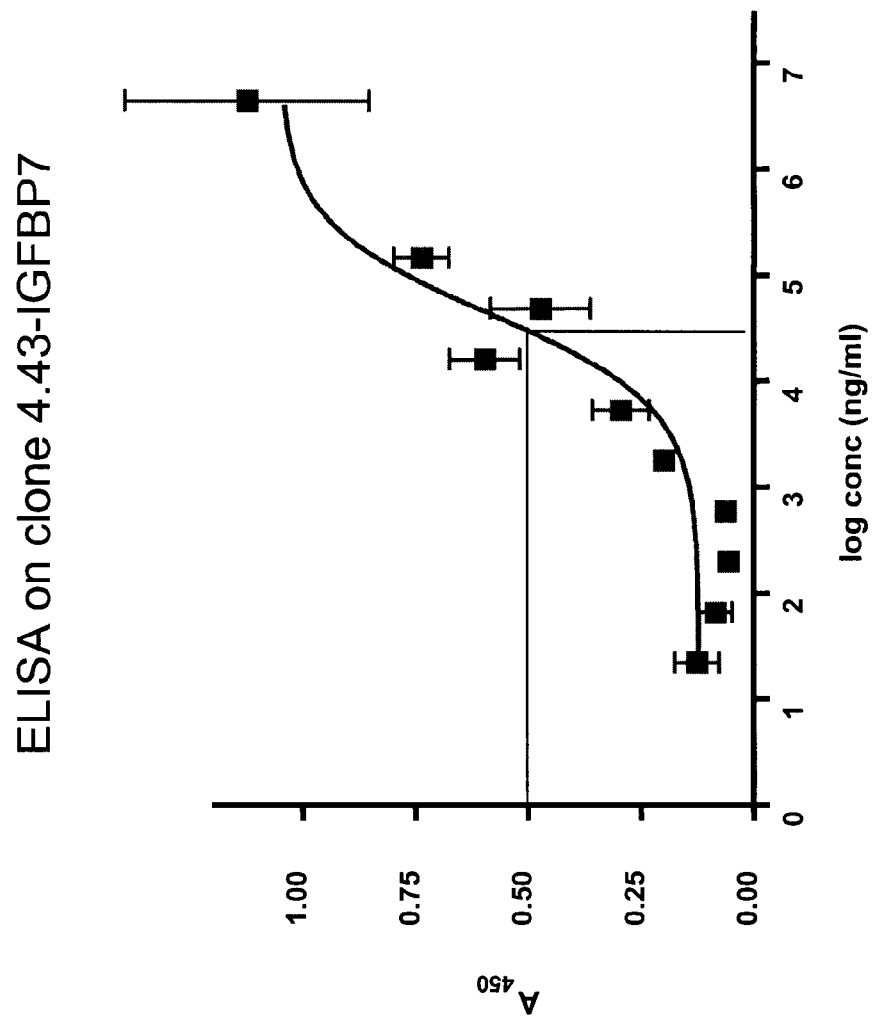
FIG. 4 shows a standard ELISA in which IGFBP7 was coated on microtitre plates, and binding of sdAb cone 4.43-IGFBP7 was assessed.
Figure 5:
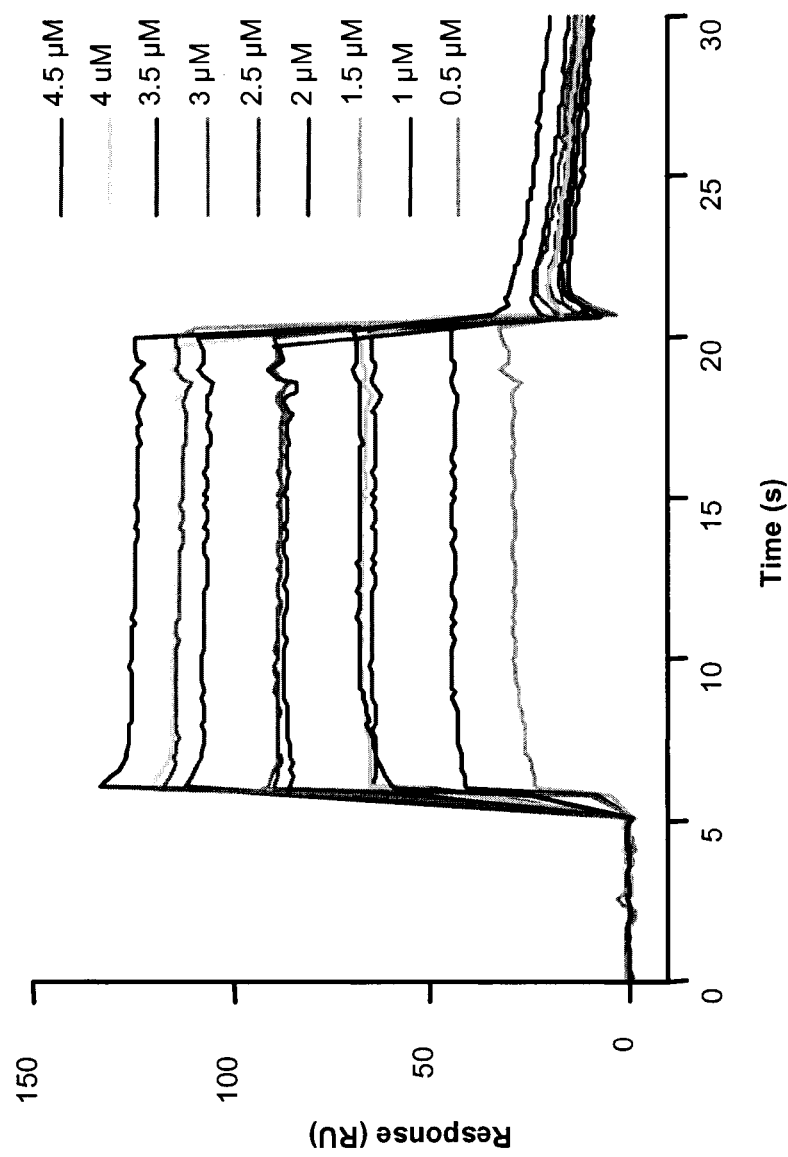
FIG. 5 shows the BiaCore analysis of sdAb clone 4.6-IGFBP7. Sensorgram overlay showing IGFBP7-4.6 binding to immobilized IGFBP7 at concentrations of 0.5, 1, 1.5, 2, 2.5, 3, 4, and 4.5 µM sdAb.
Figure 6:
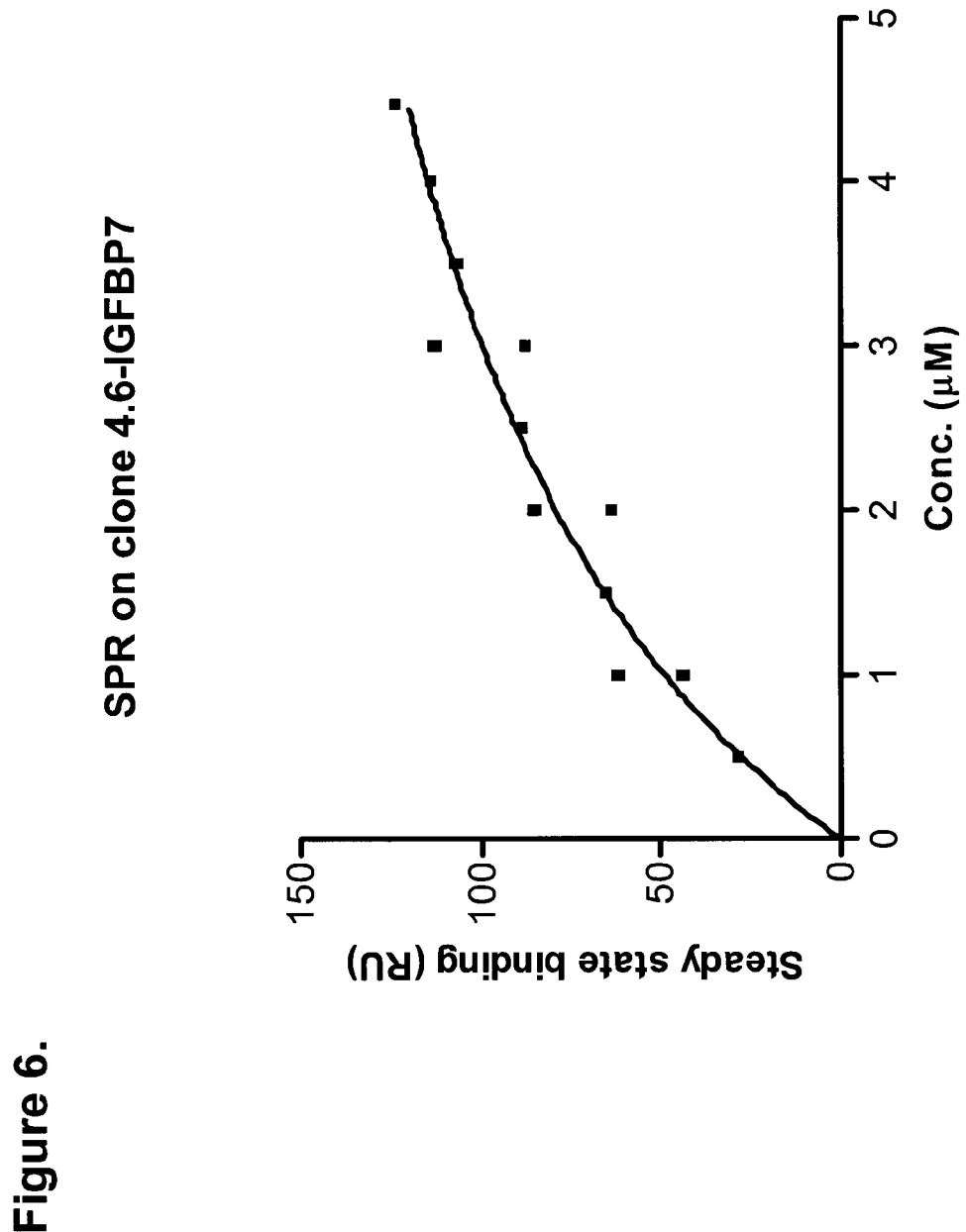
FIG. 6 shows the surface plasmon resonance analyses of sdAb clone 4.6-IGFBP7 binding to IGFBP7. Fitting of the data to a steady state model estimates affinity of ~1 µM.
Figure 7:
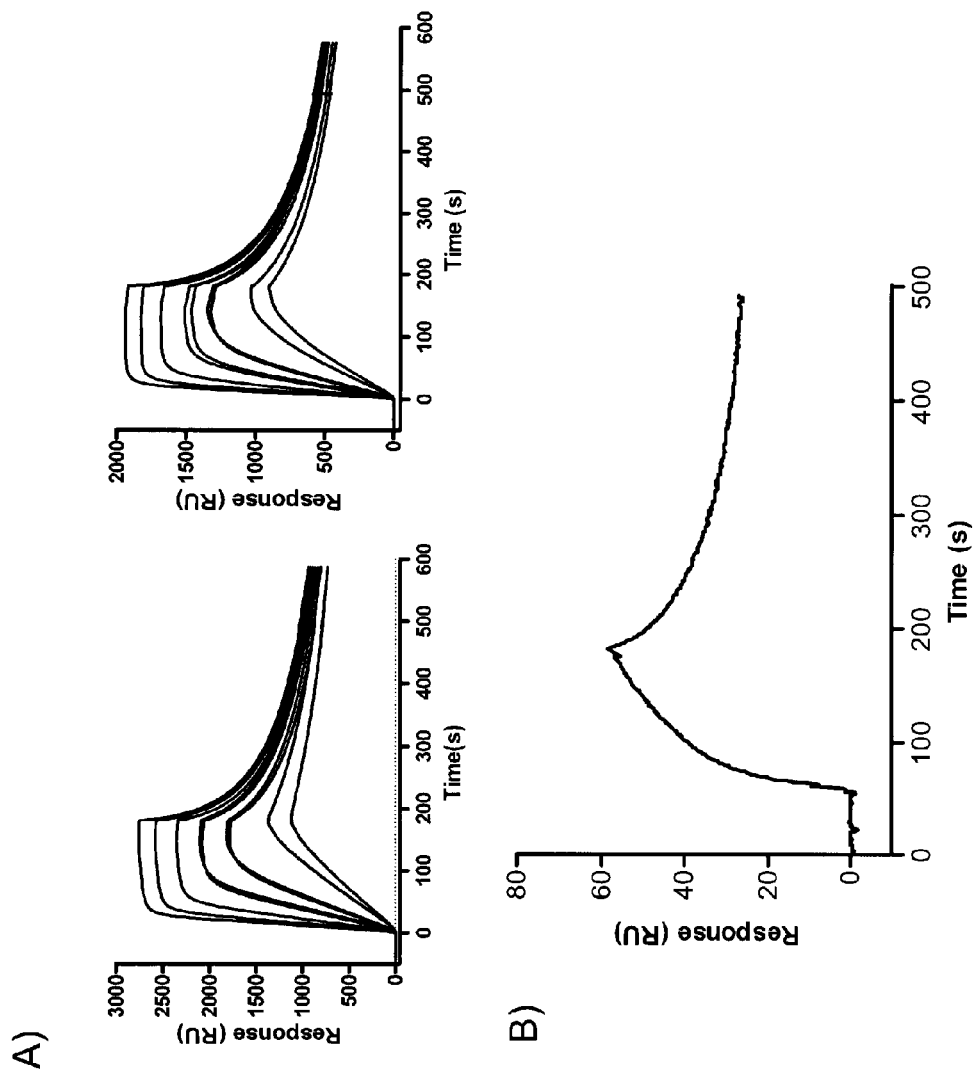
FIG. 7 shows the BiaCore analysis of sdAb clone 4.43-IGFBP7.

The present invention relates to isolation of single domain antibodies against IGFBP7 that specifically target glioblastoma tumor vessels, and to their use as diagnostic tools for detecting neoplastic diseases and as therapeutic agents for reducing tumor angiogenesis.

The present invention provides an isolated or purified antibody or fragment thereof, comprising:
  the sequence of complementarity determining region (CDR) 1 selected from sequences comprising RTFSRLAM (SEQ ID NO:3) and RTSRRYAM (SEQ ID NO:6);
  the sequence of CDR2 comprising GISRSGDGTHYAYSV (SEQ ID NO:4); and
  the sequence of CDR3 selected from sequences comprising AARTAFYYYGNDYNY (SEQ ID NO:5) and AAARTAFYYYGNDYNY (SEQ ID NO:7), wherein the antibody or fragment thereof binds to Insulin-like Growth Factor Binding Protein 7 (IGFBP7).

The term "antibody", also referred to in the art as "immunoglobulin" (Ig), used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen binding determinants of the molecule, and thus determines the specificity of an antibody for its target antigen.

The majority of sequence variability occurs in the "complementarity-determining regions" (CDRs). There are six CDRs total, three each per variable heavy and light chain; the CDR combine to form the antigen-binding site, and contribute to binding and recognition of an antigenic determinant. The region outside of the CDRs is referred to as the framework region (FR). This characteristic structure of antibodies provides a stable scaffold upon which substantial antigen-binding diversity can be explored by the immune system to obtain specificity for a broad array of antigens[1].

An "antibody fragment" as referred to herein may include any suitable antigen-binding antibody fragment known in the art. The antibody fragment may be obtained by manipulation of a naturally-occurring antibody, or may be obtained using recombinant methods. For example, an antibody fragment may include, but is not limited to Fv, single-chain Fv (scFV; a molecule consisting $V_L$ and $V_H$ connected with a peptide linker), Fab, Fab$_2$, single domain antibody (sdAb), and multivalent presentations of these.

The antibody fragment may be a single domain antibody (sdAb), which is derived from heavy chain antibodies of camelid origin[2]. These antibodies lack light chains and thus their antigen binding sites consist of one domain, termed $V_H$H. sdAbs have also been observed in shark and are termed VNARs[3], and may be engineered based on human heavy chain sequences[4, 5]. As used herein, sdAb includes those directly isolated from $V_H$, $V_H$H or $V_{NAR}$ reservoir of any origin through phage display or other display technologies and those generated through further modification of such sdAbs by humanization, affinity maturation, stabilization and other way of antibody engineering. The term also includes homologues, derivatives, or fragments that are capable of functioning as a single-domain antibody domain.

A person of skill in the art would be well-acquainted with the structure of a single-domain antibody (see, for example, 3DWT, 2P42 in protein data bank). Most notably, an sdAb comprises a single immunoglobulin domain, therefore only three CDRs form the antigen-binding site. However, not all CDRs may be required for binding the antigen. For example, and without wishing to be limiting, one, two, or three of the CDRs may contribute to binding and recognition of the antigen by the sdAb of the present invention. The CDRs of the sdAb are referred to herein as CDR1, CDR2, and CDR3.

The antibody or fragment thereof of the present invention exhibit a binding affinity for insulin-like growth factor binding protein-7 (IGFBP7), a cell-adhesive glycoprotein found in endothelial cells and in certain tumor cell populations. The binding of the antibody or fragment thereof of the present invention to IGFBP7 may inhibit angiogenesis in brain endothelial cells associated with cancer cells. Characteristics of IGFBP7 are well-known to those of skill in the art.

In one non-limiting embodiment, the antibody or fragment thereof may have a CDR1 of sequence RTFSRLAM (SEQ ID NO:3) and RTSRRYAM (SEQ ID NO:6); CDR2 of sequence GISRSGDGTHYAYSV (SEQ ID NO:4); and CDR3 of sequence AARTAFYYYGNDYNY (SEQ ID NO:5) and AAARTAFYYYGNDYNY (SEQ ID NO:7). The antibody or fragment thereof may be an sdAb. The sdAb may be of camelid origin, and thus may be based on camelid framework regions; alternatively, the CDR may be grafted onto VNAR or human $V_H$H or $V_L$ framework regions. Thus, the present embodiment further encompasses an antibody fragment that is humanized, wherein one or more than one of the heavy chain complementary-determining regions defined herein are fused or grafted to a human variable region ($V_H$H or $V_L$). In such a case, the conformation of said one or more than one complementary-determining region is preserved, and the affinity and specificity of the sdAb for its target (i.e., IGFBP7) is also preserved. Persons of skill in the art would be amply familiar with methods of preparing such humanized antibody fragments.

In a specific, non-limiting example, the isolated or purified antibody or fragment thereof of the present invention may comprise the sequence:
AIAIAVALAGFATVAQAQVKLEESGGGS-
VQPGGSLRLSCAASGRTFSRLAMGWFRQ APGK-
ERELVAGISRSGDGTHYAYSVKGRFTIS-
RDNAANTVELQMNSLKPEDTAVYFC
AAARTAFYYYGNDYNYWGQGTQVTVSS (SEQ ID NO:1; also referred to herein as clone 4.6-I), or a sequence substantially identical thereto.

In another example, the sequence of the antibody or fragment thereof may comprise the sequence:
AIAIAVALAGFATVA-
QAQVKLEESGGGLVQAGGSLRLSCAAS-
GRTSRRYAMGWFRQ APGKEREFVAGISRSGDGTH-
YAYSVKGRFTISRDNAANTVELQMNSLKPEDTAVY
FC AAARTAFYYYGNDYNYWGQGTQVTVSS (SEQ ID NO. 2; also referred to herein as clone 4.43-I), or a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at http://ca.expasy.org/tools/blast/), BLAST-P, Blast-N, or FASTA-N, or any other appropriate software that is known in the art.

The substantially identical sequences of the present invention may be at least 75% identical; in another example, the substantially identical sequences may be at least 70, 75, 80, 85, 90, 95, or 100% identical at the amino acid level to sequences described herein. Importantly, the substantially identical sequences retain the activity and specificity of the reference sequence. In a non-limiting example, the percent identity between the sequences of SEQ ID NO:1 and 2 is about 95% over the length of the sequences.

The antibody or fragment thereof of the present invention may also comprise additional sequences to aid in expression, detection or purification of a recombinant antibody or fragment thereof. For example, and without wishing to be limiting, the antibody or fragment thereof may comprise a targeting or signal sequence (for example, but not limited to ompA), a detection tag (for example, but not limited to c-Myc), a purification tag (for example, but not limited to a histidine purification tag), or a combination thereof.

The antibody or fragment thereof of the present invention may also be in a multivalent display. Multimerization may be achieved by any suitable method of know in the art. For example, and without wishing to be limiting in any manner, multimerization may be achieved using self-assembly molecules[6, 7], as described in WO2003/046560. The described method produces pentabodies by expressing a fusion protein comprising the antibody or fragment thereof and a pentamerization domain, which assembles into a pentamer, through which a multivalent display of the antibody or fragment thereof is achieved. Each subunit of the pentamer may be the same or different. Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection[8], c-jun/Fos interaction, "Knob into holes" interaction[10].

The also present invention provides anti-IGFBP7 antibodies or fragments thereof conjugated to a molecule selected from the group consisting of cytotoxic agents, cytostatic drugs and glycoproteins. The molecule may be conjugated to the antibody by any suitable method known in the art; for example, and without wishing to be limiting in any manner, the conjugation may be by recombinant expression or by chemical linkage. Those of skill in the art would be familiar with methods suitable for preparing conjugates of the present invention.

The present invention also encompasses nucleic acid sequences encoding the molecules as described herein. The nucleic acid sequence may be codon-optimized. The present invention also encompasses vectors comprising the nucleic acids as just described. Furthermore, the invention encompasses cells comprising the nucleic acid and/or vector as described.

The present invention further provides detectably labelled anti-IGFBP7 antibody clone 4.6 and clone 4.43; such detectable label, also referred to herein as detectable marker, may selected from the group consisting of radiochemicals, optical contrast probes, and/or MRI contrast probes (for diagnostic imaging); these may include, but are not limited to radioisotopes, florochromes, dyes, enzymes and biotin. Persons of skill in the art would be familiar with suitable specific detectable labels, based on the application desired; methods of detecting the labels would also be known to skilled persons.

Also provided by the present invention is a method for detecting IGFBP7 in a biological sample comprising the steps of (a) exposing a sample suspected of containing IGFBP7 to a detectably labelled anti-IGFBP7 antibody; (b) washing the sample; and (c) detecting the presence of the detectably labelled anti-IGFBP7 antibody in the sample. The biological sample can be selected from the group consisting of a solution containing blood cells or tissue cells or a solid tissue specimen. The cells are selected from the group consisting of brain, lung, colon, pancreas, stomach, breast tissue specimens.

The present invention also provides a method for diagnosing diseases characterized by proliferation of endothelial cells, comprising the steps of (a) obtaining a tissue sample from a patient suspected of having a disease characterized by proliferation of endothelial cells; (b) exposing the tissue sample to a detachably labelled anti-IGFBP7 antibody; (c) washing the tissue sample; and (d) detecting the presence of the detectably labelled anti-IGFBP7 antibody in the tissue sample. Here, the disease could be selected from the group of neoplastic diseases, such as brain cancer, or diseases involving tumor angiogenesis. The disease could also be selected from the group of Grade I, II, III, IV brain gliomas.

The present invention further provides a method for imaging neovascularization in an organism, comprising the steps of (a) administering to the organism a detectably labelled anti-IGFBP7 antibody into circulation; and (b) detecting an amount of the detectably labelled anti-IGFBP7 antibody which binds to the site of neovascularization. The step of administering may comprise systemic intravenous, intraperitoneal, subcutaneous, or intraarterial administration.

Also provided by the present invention is a method for predicting brain tumor growth by detecting or evaluating neovascularization of brain blood vessel of a subject comprising: (a) administering to the subject an effective amount of anti-IGFB7 antibody contrast agent; (b) detecting the agent thereby forming an image of the accumulated anti-IGFBP7 in the tumor vessels; and (c) predicting risk of brain tumor in the subject based on the image formed. Such prediction could be made based on a quantitative measure of the accumulation of the contrast agent in the brain tumor vessel of the subject. d) non-invasive monitoring tumor size and neovascularization in response to therapy The detection method disclosed herein could be selected from the group consisting of: x-ray imaging, computed tomography (CT), optical imaging, computed tomography angiography (CTA), electron beam (EBT), magnetic resonance imaging (MRI), magnetic resonance angiography (MRA), and positron emission tomography, gamma camera or with SPECT.

Methods for alleviating the symptoms of a disease characterized by abnormal growth of endothelial cells are also provided by the present invention. Such methods may comprise the step of administering the pharmaceutical composition of an agent having a binding affinity for IGFBP7 to a patient suspected of having a disease characterized by abnormal growth of endothelial cells.

Thus, the present invention enables a person of skill in the art to utilize an antibody or fragment thereof of the present invention, for example an anti-IGFBP7 single domain antibody and/or a conjugate thereof, in the following areas of application:

in vivo imaging/diagnosis of brain tumors;
diagnosis of brain tumor invasiveness based on immunohistochemical evaluation of IGFBP7 expression in tumor vessels;
anti-angiogenic (function-modulating) properties of anti-IGFBP7 single-domain antibodies;
application of anti-IGFBP7 sdAbs in treatment of brain tumors,
and other applications that may benefit from the use of the present antibodies or fragments.

According to the invention, single domain antibodies against IGFBP7 that specifically target glioblastoma tumor vessels were isolated. The method of raising anti-IGFBP7 single domain antibodies is described and the antibody clones 4.6 and 4.43 are provided. Binding characteristics of these clones to IGFBP7 are described (FIGS. 1-7).

Figure 8:
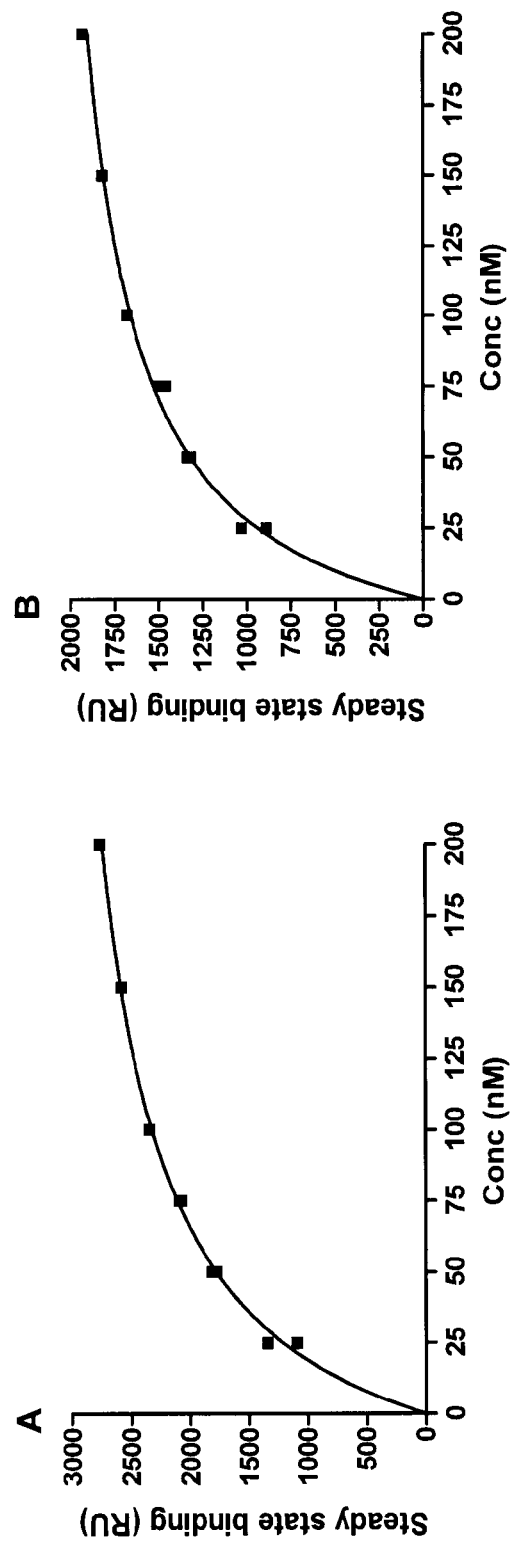
FIG. 8 shows the steady state analysis of anti-IGFBP7-4.43 monomer. Anti-IGFBP7-4.43 was used at 25, 25, 50, 50, 75, 75, 100, 150, and 200 nM. The left panel shows results where the ligand is recombinant protein IGFBP7 from R&D ($K_D$ (M): $4\times10^{-8}$), while the right panel shows results using recombinant custom-synthesized IGFBP7 ($K_D$ (M): $3\times10^{-8}$).
Figure 10:
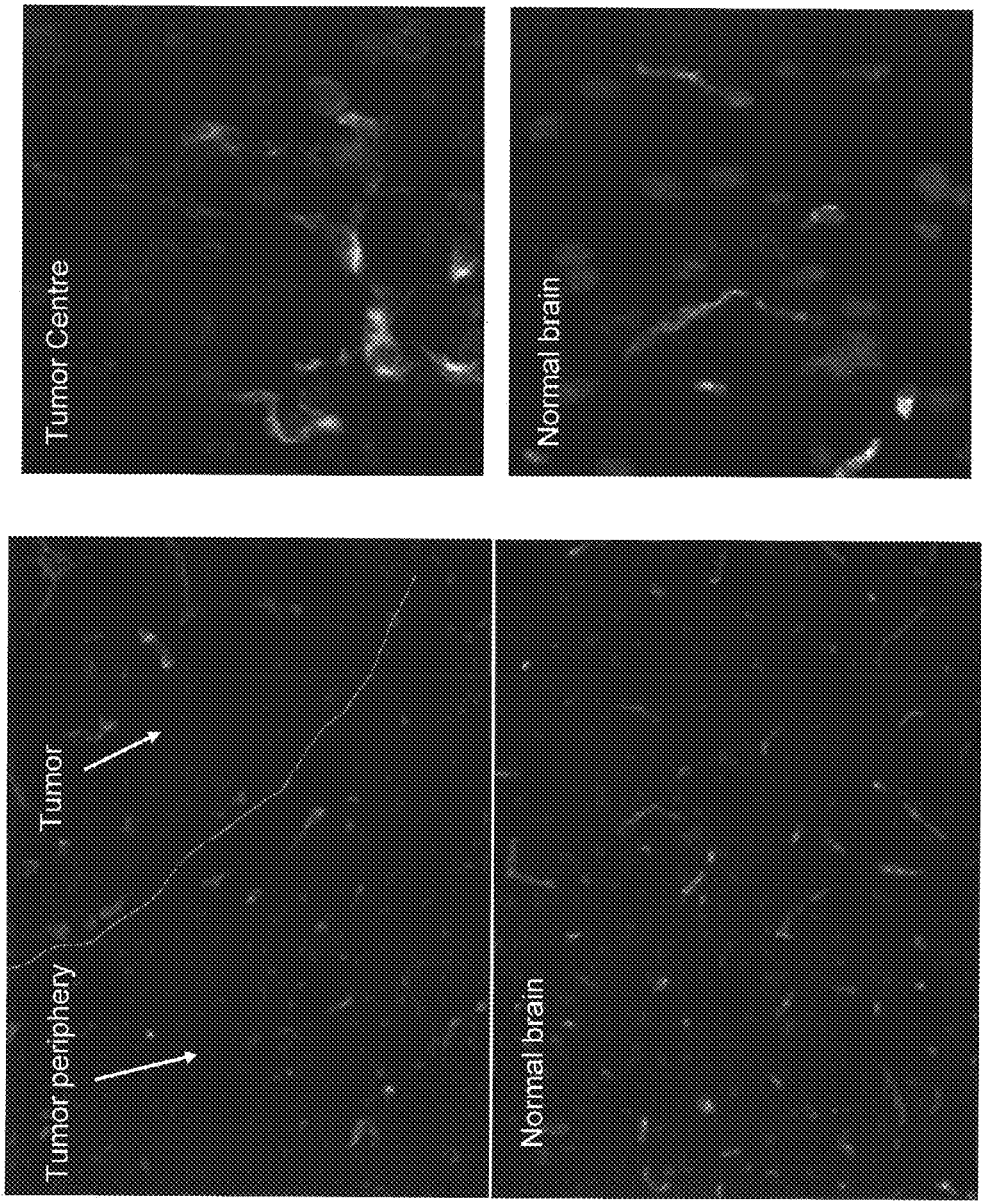
FIG. 10 shows the IGFBP7 expression (determined by immunofluorescence using a commercial anti-IGFBP7 antibody) in vessels of normal brain and orthotopic brain tumor (human glioblastoma cells U87MG implanted into the brain of nude mice)
Figure 11:
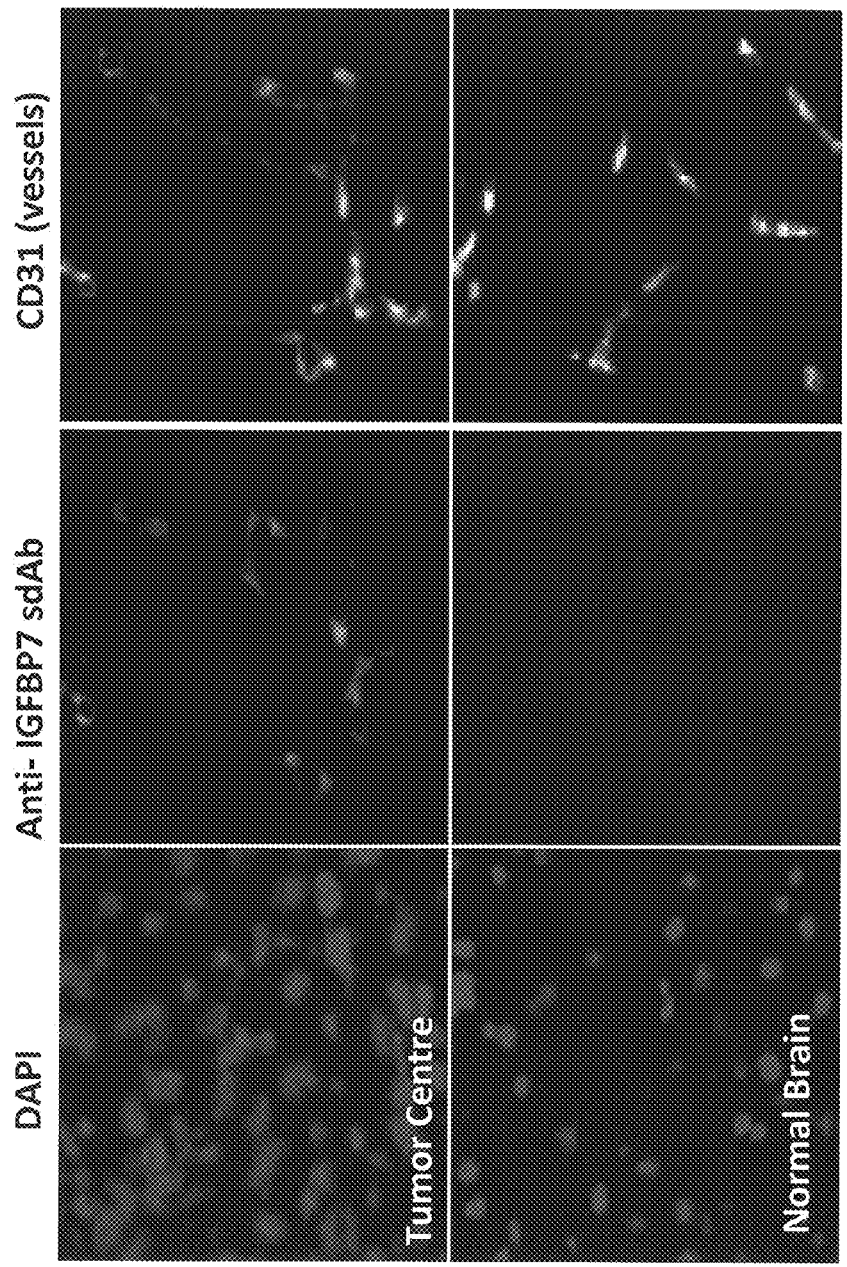
FIG. 11 shows immunostaining of the orthotopic brain tumor sections and normal mouse brain with the clone 4.43 IGFBP7 single-domain antibody and the vascular marker, CD31.
Figure 12:
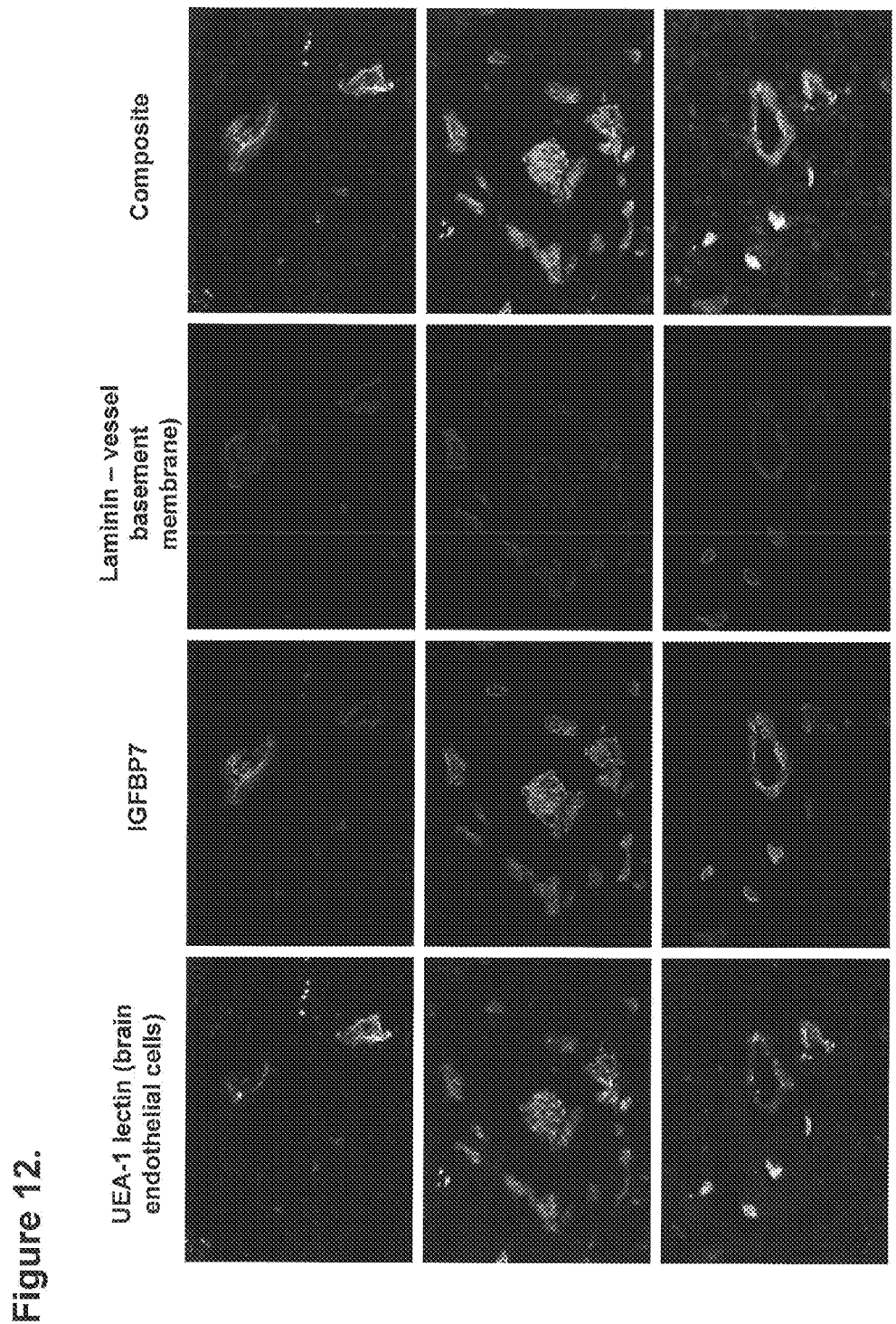
FIG. 12 shows the IGFBP7 expression in vessels of surgically-removed human glioblastoma tumors (determined using immunofluorescence with commercial IgG antibody).
Figure 13:
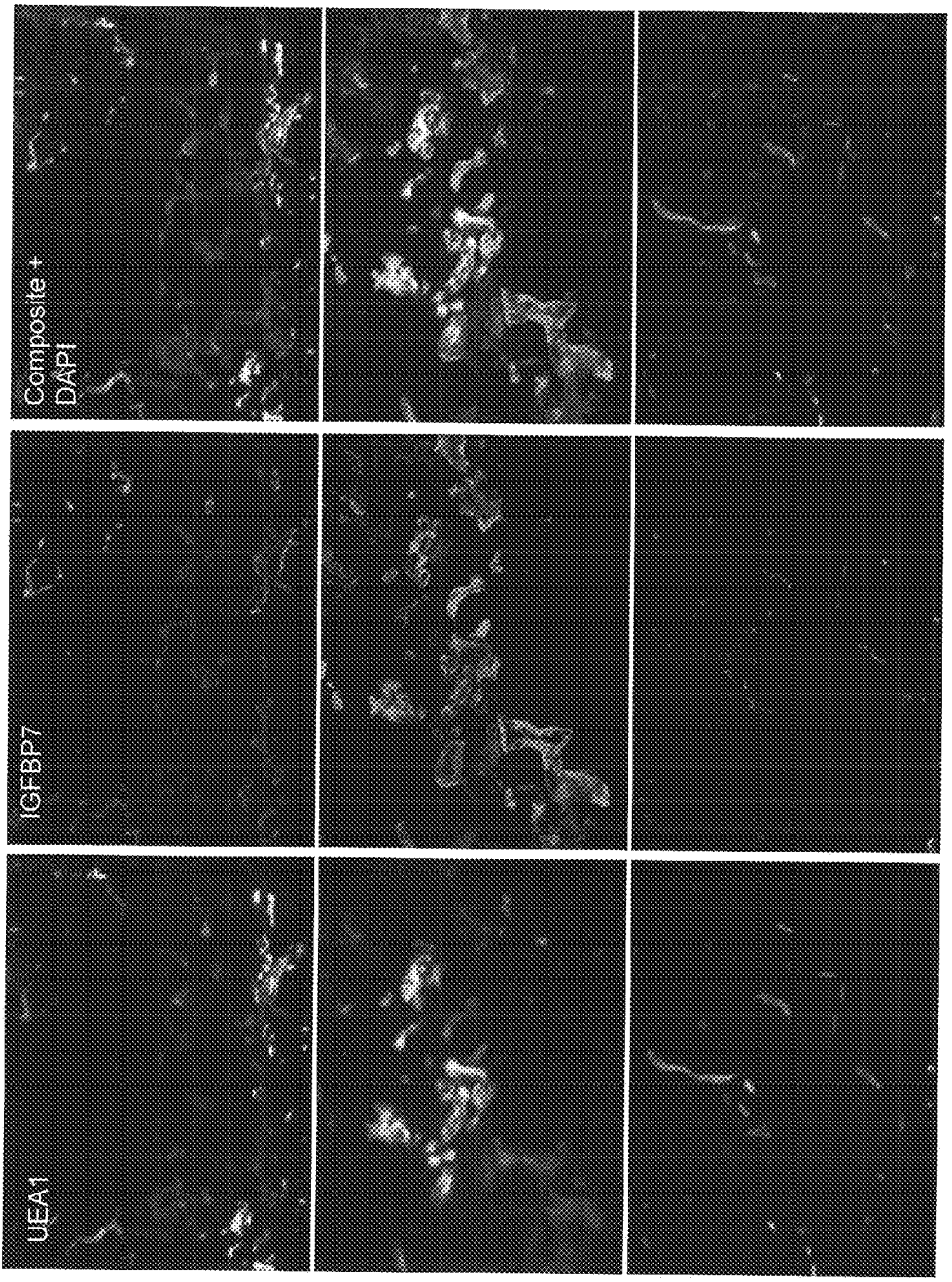
FIG. 13 shows the IGFBP7 expression in vessels of surgically-removed human glioblastoma tumors detected using clone 4.43-IGFBP7
Figure 14:
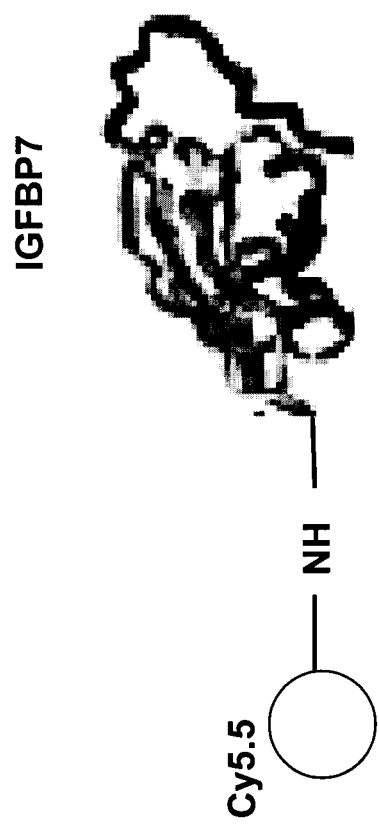
FIG. 14 shows a schematic drawing of clone 4.43-IGFBP7 conjugation to fluorophore Cy5.5, useful for in vivo non-invasive imaging of animals.
Figure 15:
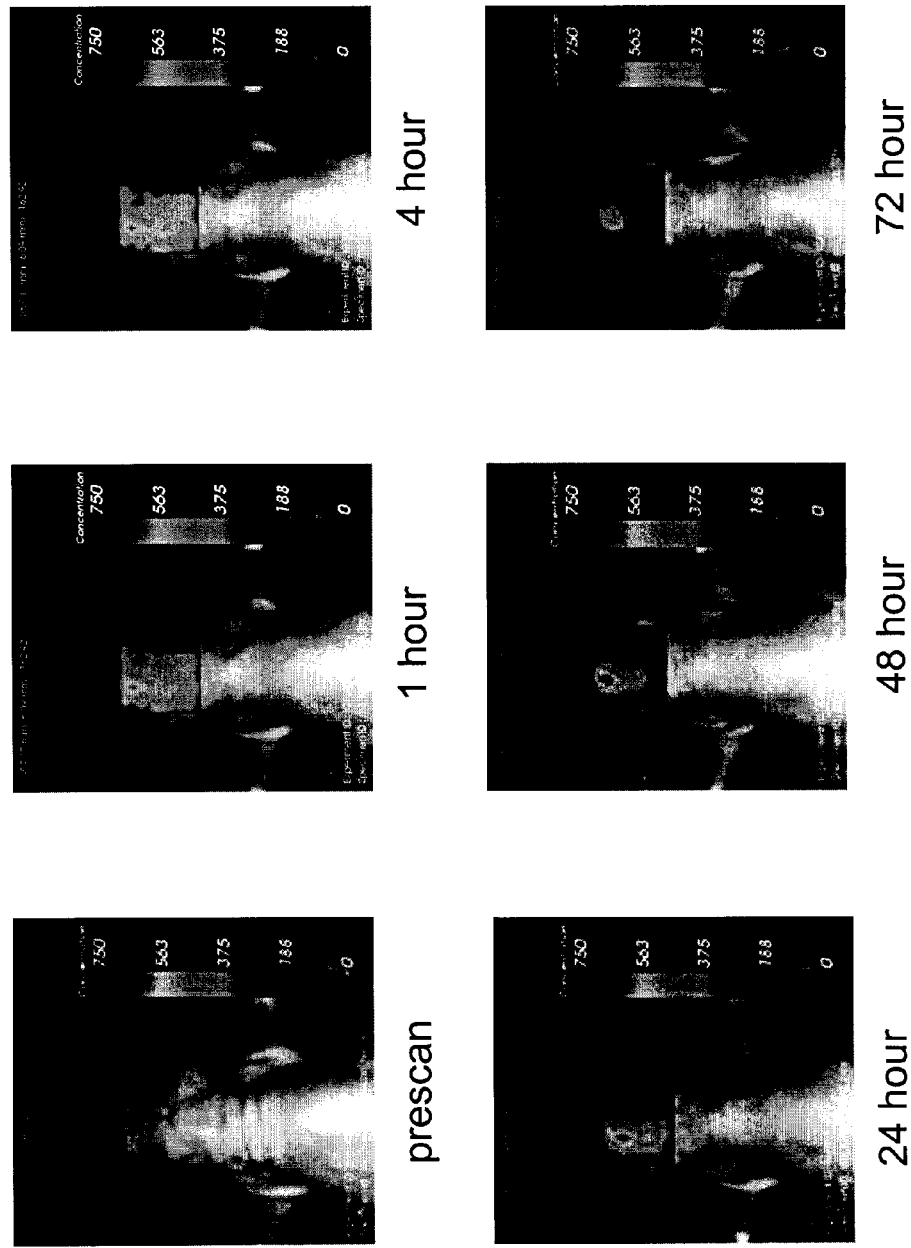
FIG. 15 shows fluorescence detection in the head of mice bearing orthotopic brain tumors at 1 h, 4 h, 24 h, 48 h, and 72 h after intravenous injection of clone 4.43 IGFBP7-Cy5.5 conjugate using in vivo optical imaging.
Figure 16:
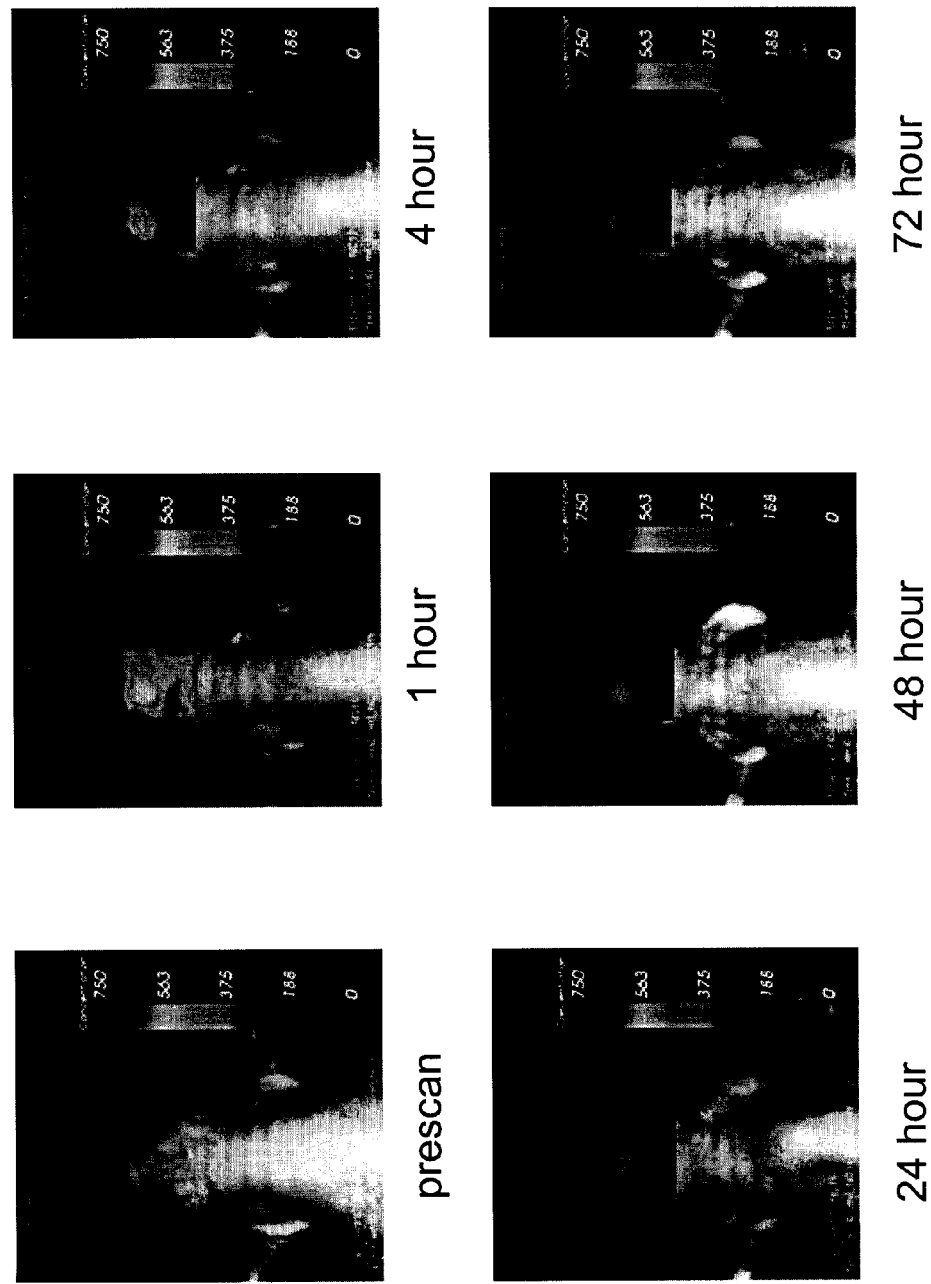
FIG. 16 shows fluorescence detection in the head of mice bearing orthotopic brain tumors at 1 h, 4 h, 24 h, 48 h, and 72 h after intravenous injection of the control single domain antibody, NC11-Cy5.5 conjugate using in vivo optical imaging.
Figure 17:
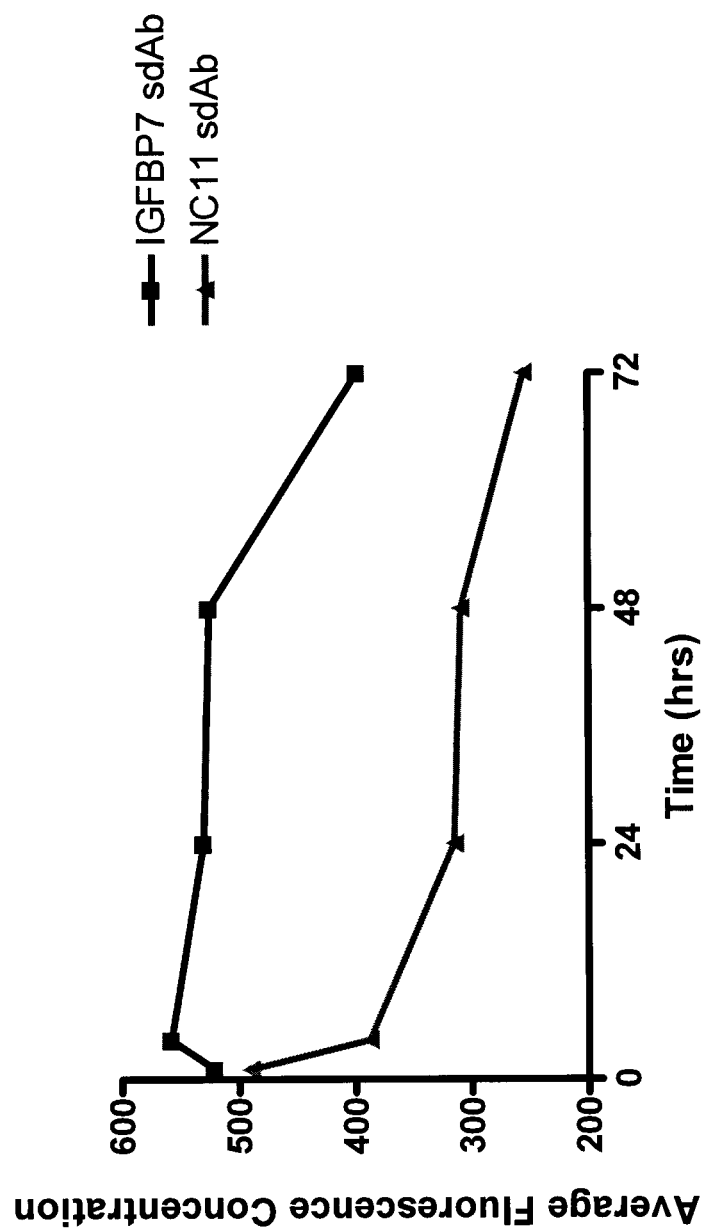
FIG. 17 shows the quantitation of time-dependent changes in the brain fluorescence concentration in animals injected with either 4.43 IGFBP7-Cy5.5 or negative control sdAb NC11-Cy5.5
Figure 18:
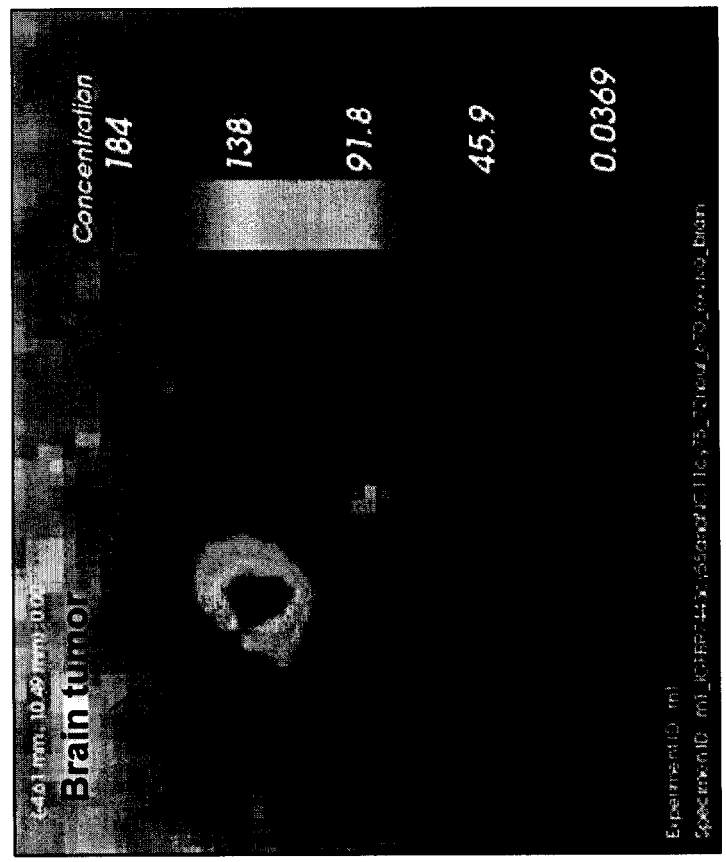
FIG. 18 shows the detection of clone 4.43 IGFBP7-Cy5.5 in the brain tumor 48 h after intravenous injection by ex vivo imaging of the dissected brain.
Figure 19:
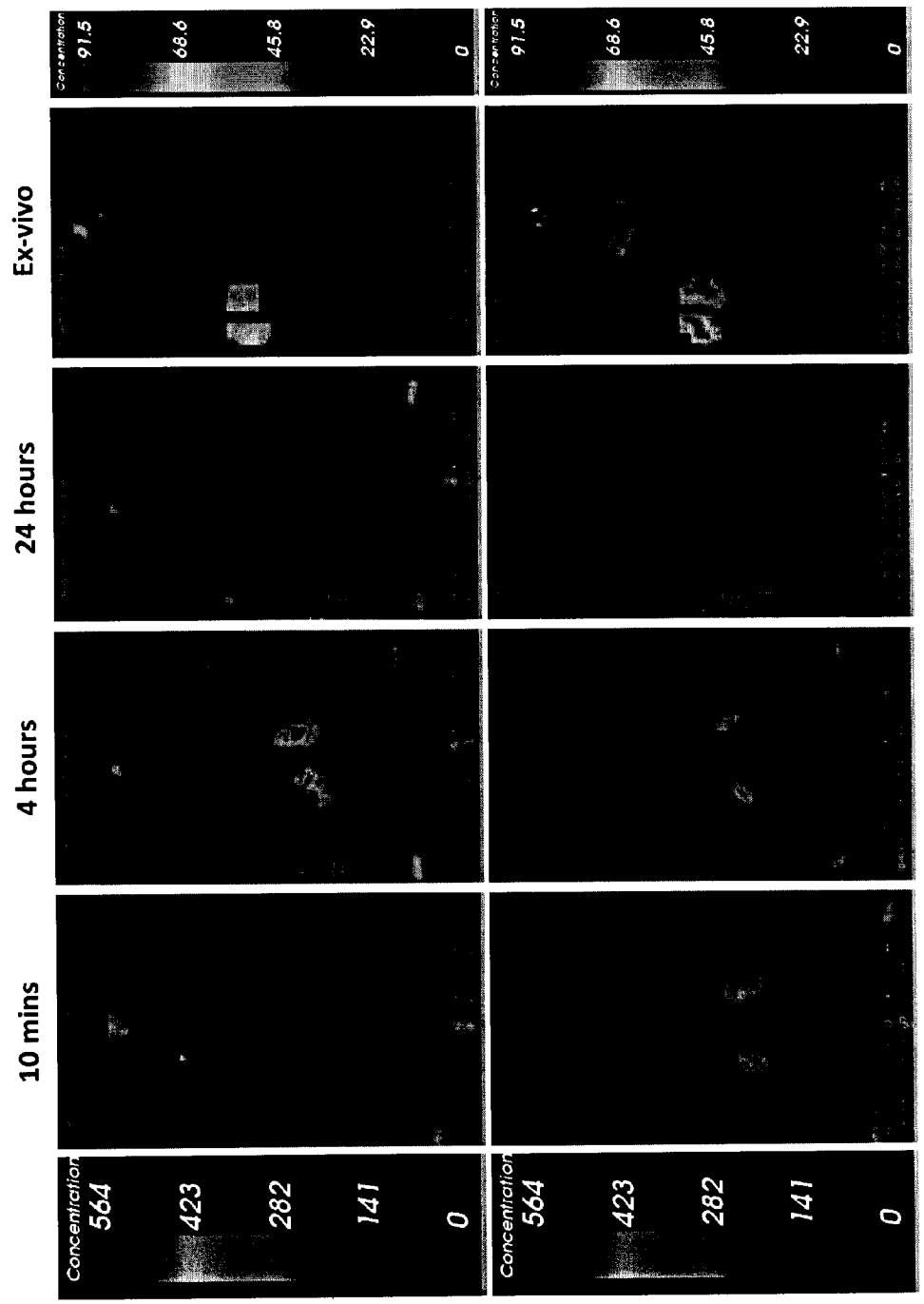
FIG. 19 shows a whole body (dorsal) imaging scans of mice bearing orthotopic brain tumor, at different time points after i.v. injection of monomeric 4.43 IGFBP7-Cy5.5 compared to negative control single domain antibody NC 11. Right panel is the ex vivo tissue imaging.
Figure 20:
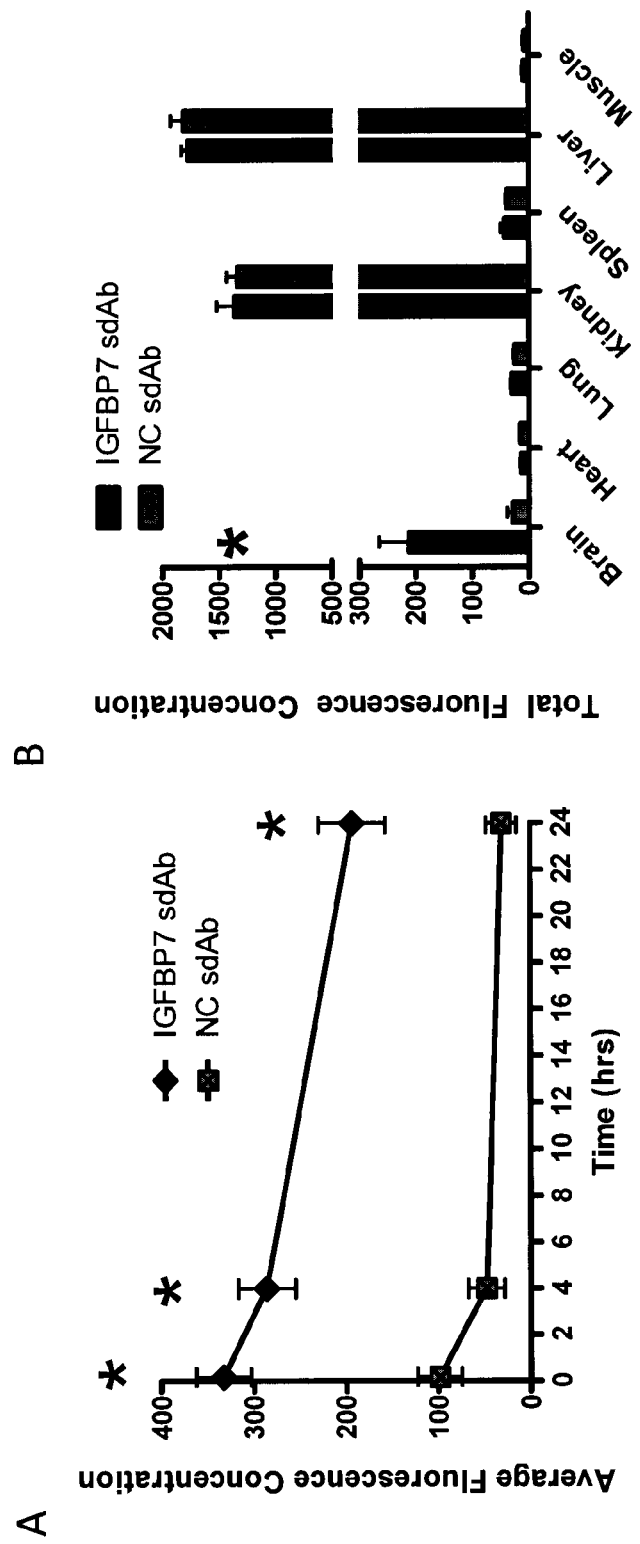
FIG. 20 (A) Anti-IGFBP7 sdAb tumor concentration over time compared to negative control (NC) sdAb. (B) Biodistribution ex-vivo at 24 hours. Data+/–SEM, n=5 per group. * indicates a statistical difference between IGFBP7 sdAb and NC sdAb group.

It is also presently described that the anti-IGFBP7 single domain antibodies are useful as diagnostic tools for detecting neoplastic diseases involving tumor angiogenesis, and a variety of other angiogenesis associated diseases. The present invention provides diagnostic methods for monitoring brain endothelial cells in brain tissue samples. The detection of angiogenic vessels using anti-IGFBP7 single domain antibodies in sections of human brain tumors (removed by surgical intervention), and in sections of experimental glioblastoma tumors (from animals injected orthotopically with U87MG glioblastoma cell) is described (FIGS. 8-10). The present invention provides a method for detecting and identifying human brain tissues undergoing neovascularization, comprising of the following steps: (a) obtaining the brain tissue sample suspected of undergoing neovascularization and (b) contacting the sample with a IGFBP7 specific sdAb under conditions suitable for forming a complex between the antibody and the IGFBP7 protein. (c) detecting the presence of any complex formed.

Furthermore, the IGFBP7 single domain antibodies are useful in molecular imaging of brain tumor blood vessels in live animals (imaging diagnostic). The ability to detect brain tumor in live experimental animals injected with glioblastoma cells using single-domain IGFBP7 antibodies conjugated with contrast agent is described. It is a further object of the present invention to provide clinical detection methods (diagnostic imaging) describing the state of brain endothelial cells growth and methods for detecting endothelial and thus vascular growth in an organism in vivo (FIGS. 11-21). Single domain antibodies, and specifically single domain antibodies designated clones 4.6 and 4.43, labelled with a detectable marker are also provided.

The disclosed antibodies are useful as therapeutic agents. Humanized single domain antibodies of the present invention can be useful in treating brain tumors by administration of a therapeutically effective amount of an anti-cancer therapeutic agent conjugated to anti-IGFBP7 antibody to patients suffering from brain cancer. Examples of such therapeutic agents include IGFBP7 antibody coupled to the radioisotope 90Y or to a toxin conjugates such as ricin.

Figure 21:
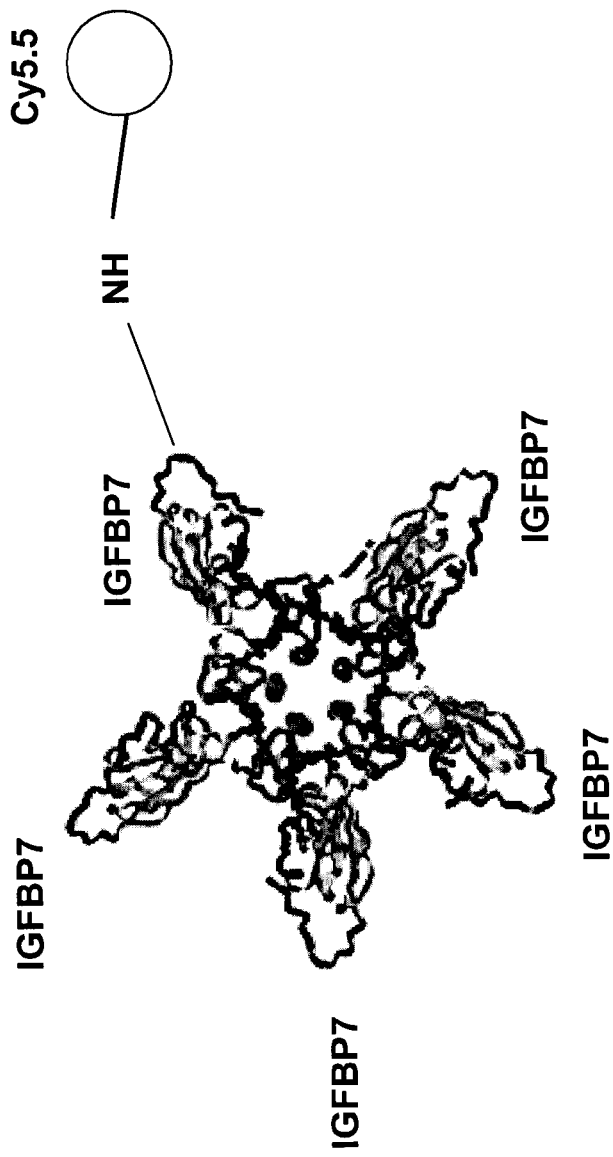
FIG. 21 shows a schematic drawing of pentamerization of the clone 4.43 IGFBP7 and its conjugation with the near-infrared fluorescence dye, Cy5.5.
Figure 22:
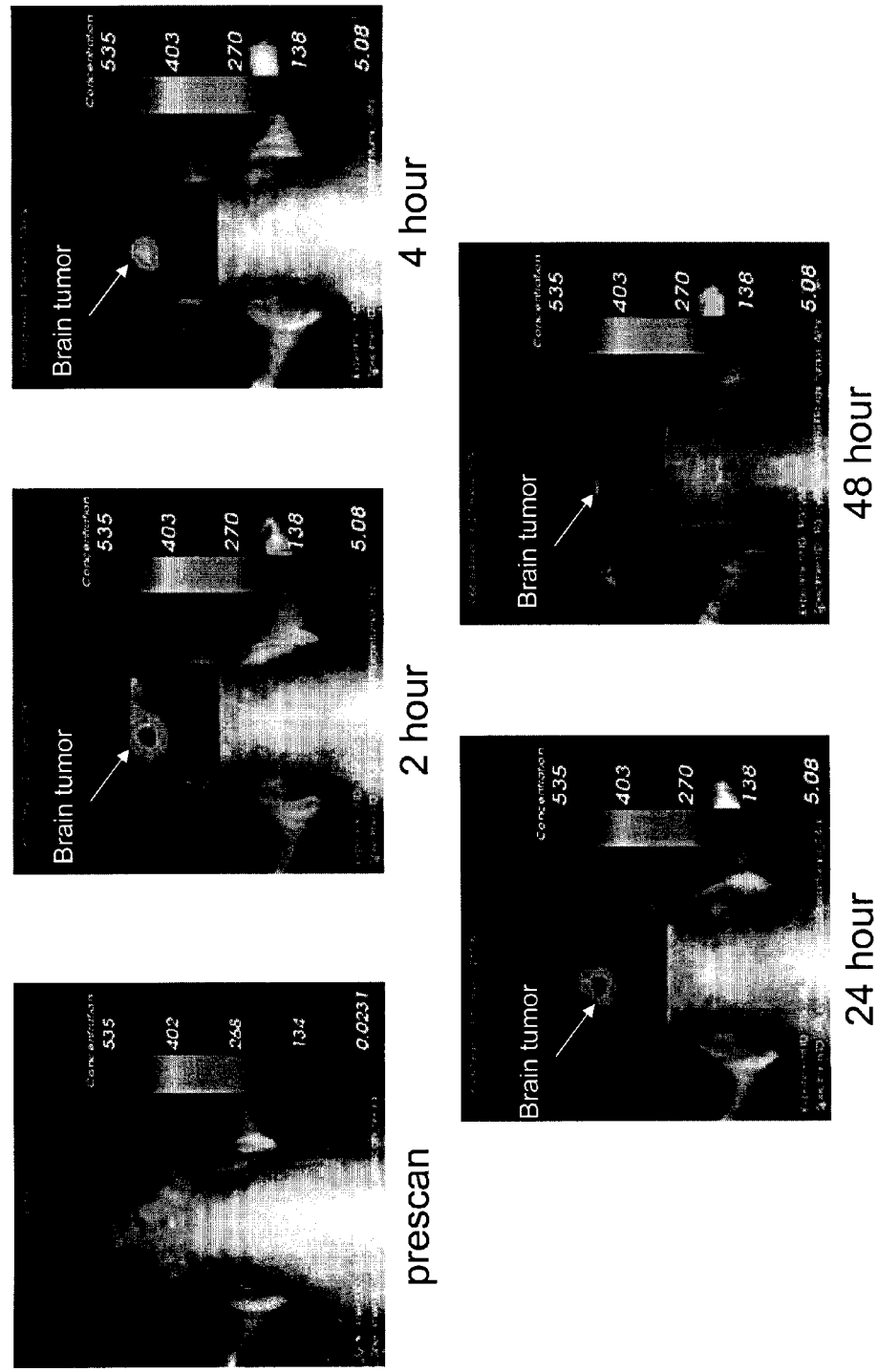
FIG. 22 shows fluorescence detection in the head of mice bearing orthotopic brain tumors at 2 h, 4 h, 24 h and 48 h, after intravenous injection of pentamerized clone 4.43 IGFBP7-Cy5.5 conjugate using in vivo optical imaging.
Figure 23:
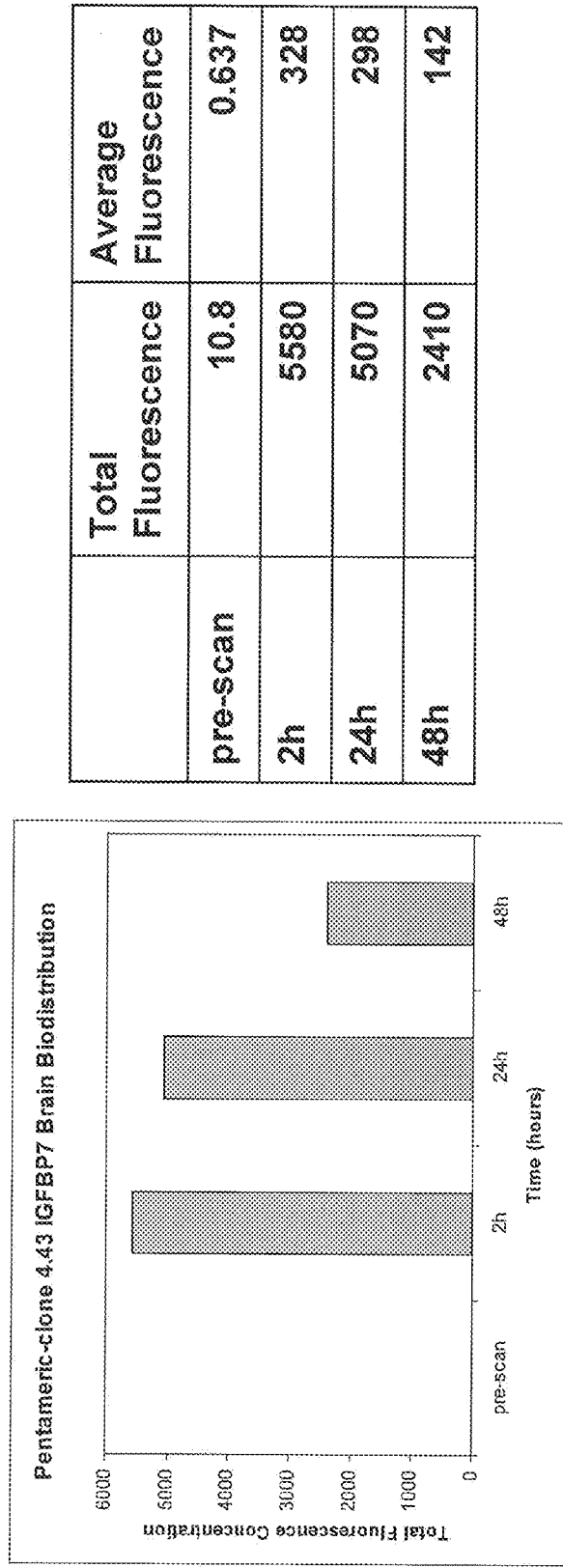
FIG. 23 shows the quantitation of temporal changes in the brain fluorescence concentration in animals injected with pentameric 4.43 IGFBP7-Cy5.5.
Figure 25:
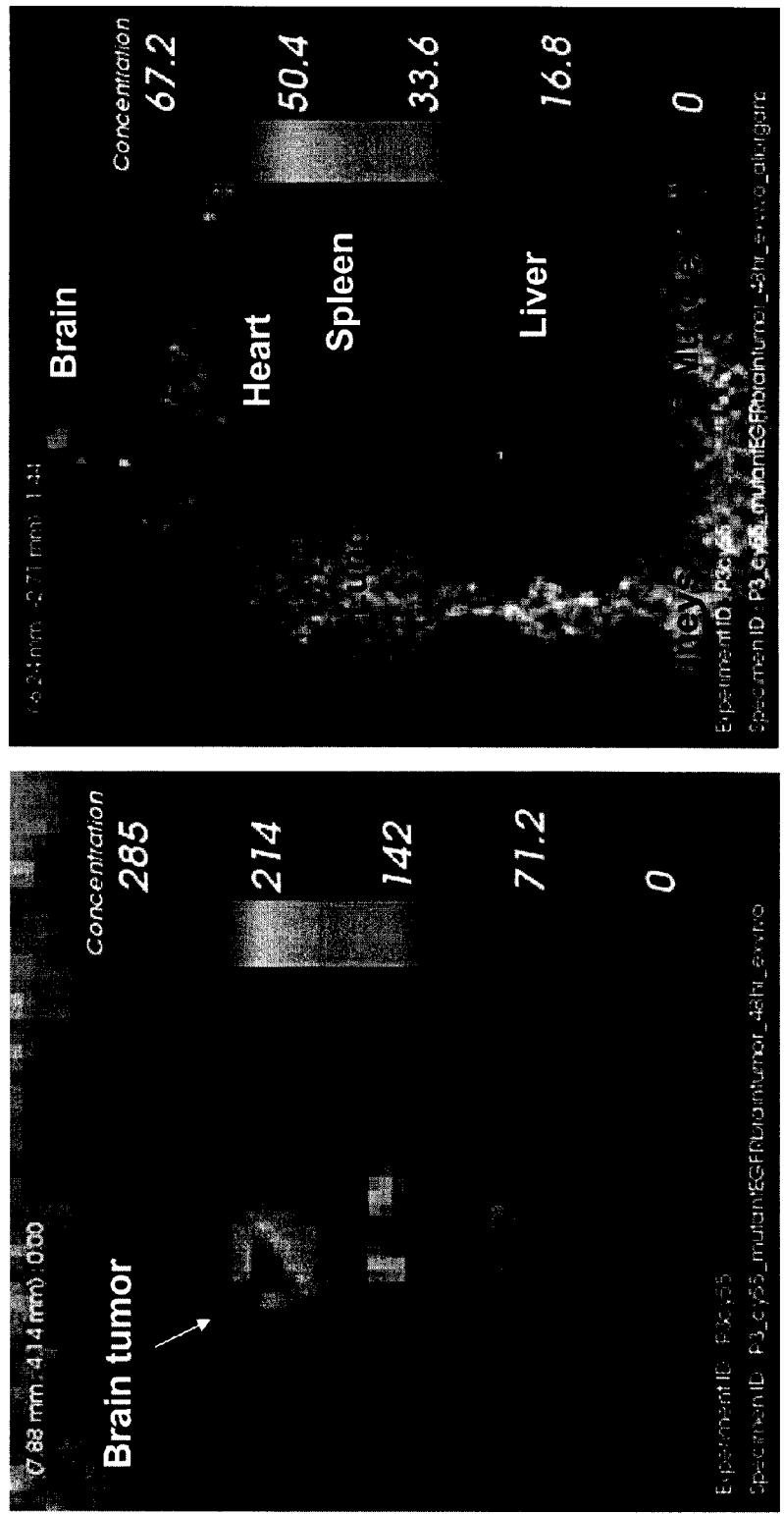
FIG. 25 ex vivo imaging of organs removed from animals after perfusion, 48 h after i.v. injection of 4.43 IGFBP7-Cy5.5.
Figure 26:
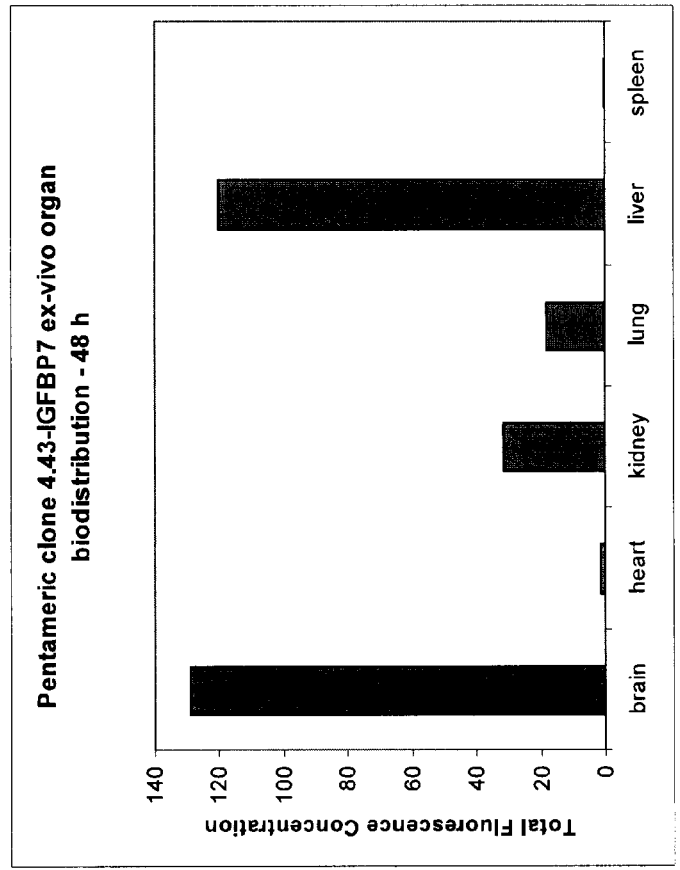
FIG. 26 shows the quantitation of the fluorescence concentration in organs 48 h after i.v. injection of 4.43 IGFBP7-Cy5.5.
Figure 27:
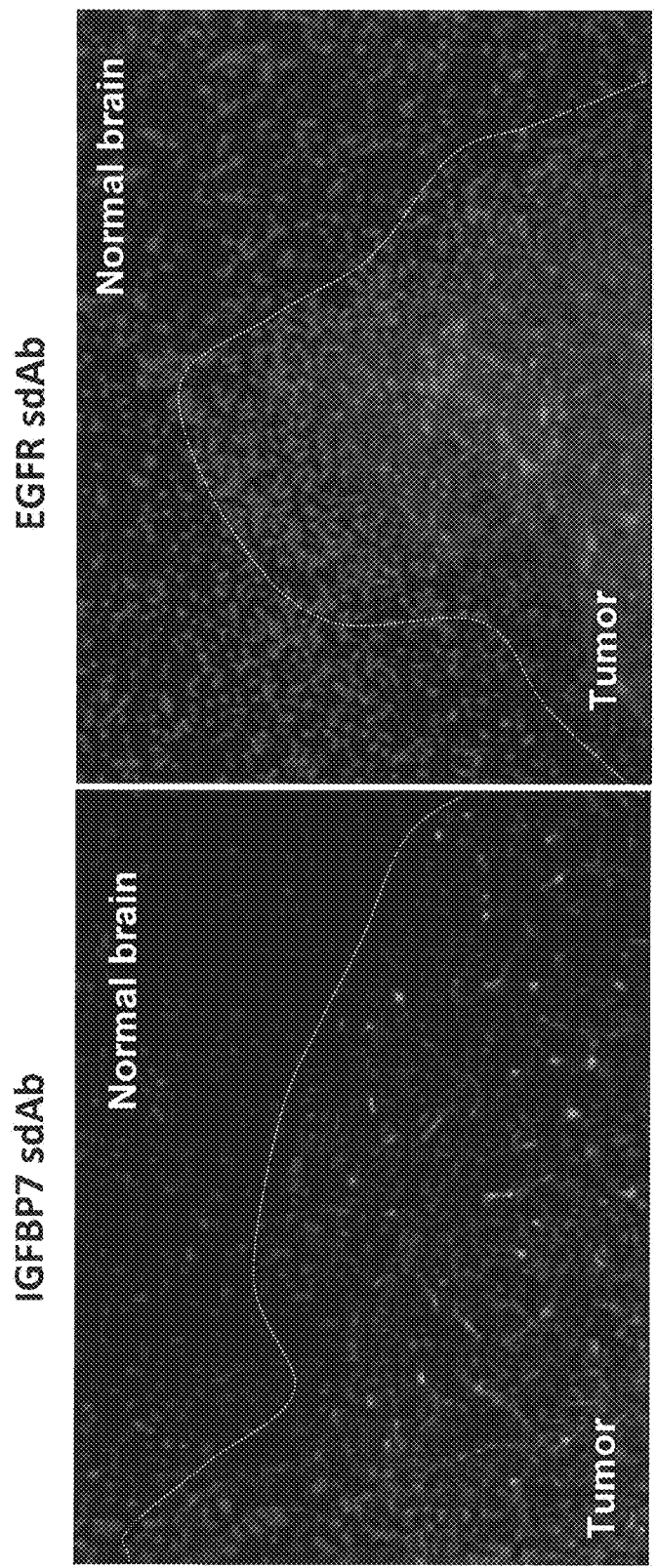
FIG. 27 shows accumulation of clone 4.43-IGFBP7 sdAb in brain tumor vessels in mice bearing orthotopic brain tumor 24 h after intravenous injection. In contrast, single-domain antibody against EGFR accumulates in the brain tumor parenchyma after i.v. injection.
Figure 28:
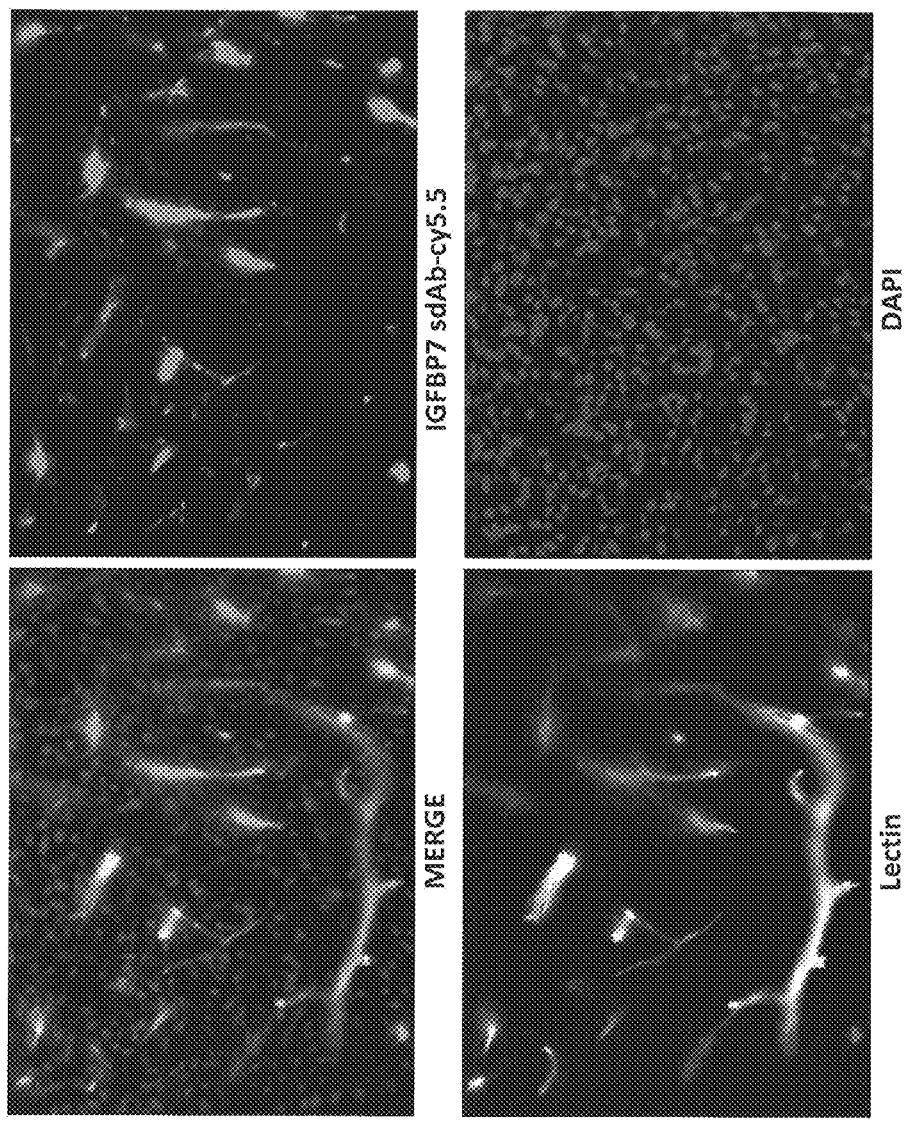
FIG. 28 shows accumulation (binding) of clone 4.43 IGFBP7 sdAb in brain tumor vessels (labeled with Tomato lectin) in mice bearing orthotopic brain tumor 24 h after intravenous injection
Figure 29:
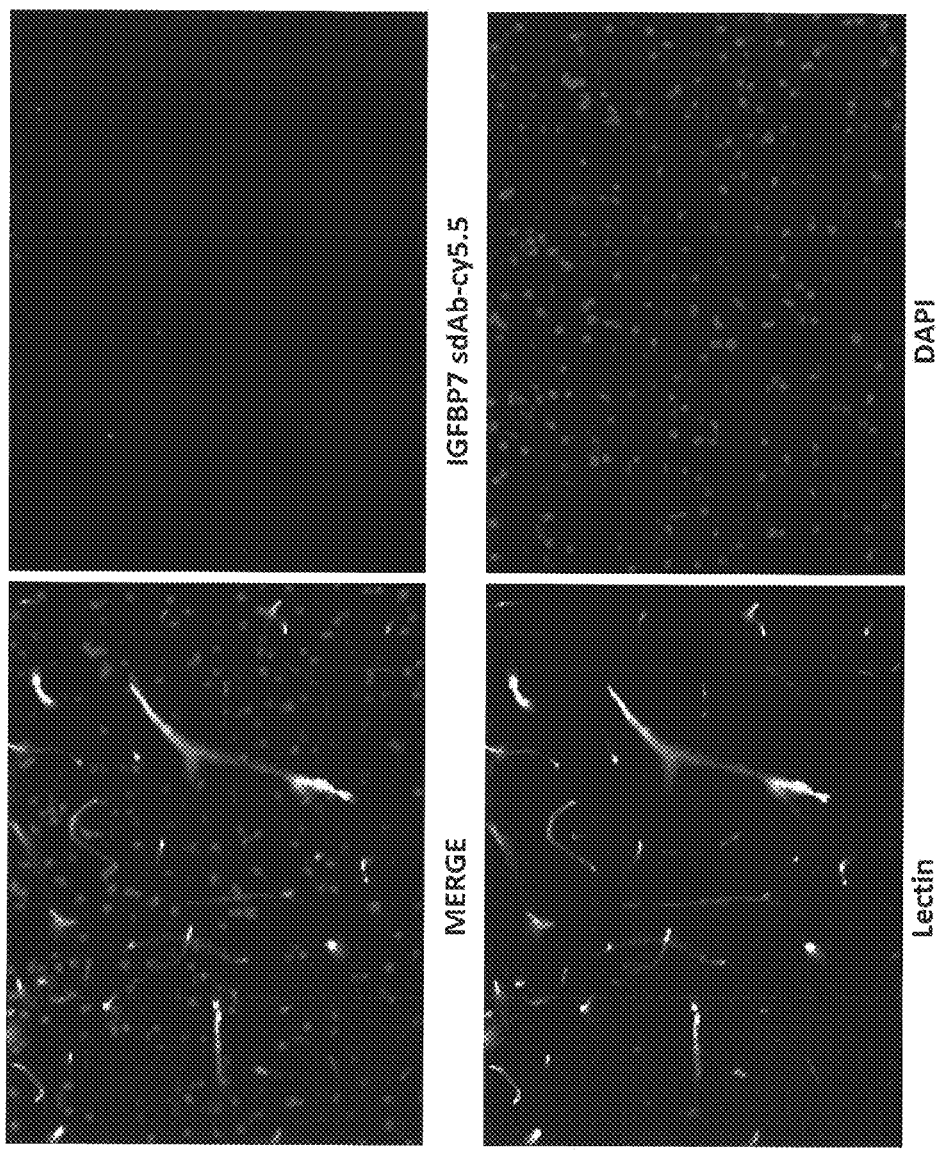
FIG. 29 shows no accumulation (binding) of clone 4.43 IGFBP7 sdAb in brain vessels (labeled with Tomato lectin) in the normal brain vessels in the contralateral tumor-free hemisphere 24 h after intravenous injection FIG. 30 demonstrates anti-angiogenic effect of the pentameric 4.43 IGFBP7 against IGFBP7- or glioblastoma cell U87MG-induced angiogenesis in human brain endothelial cells in Matrigel.
Figure 30:
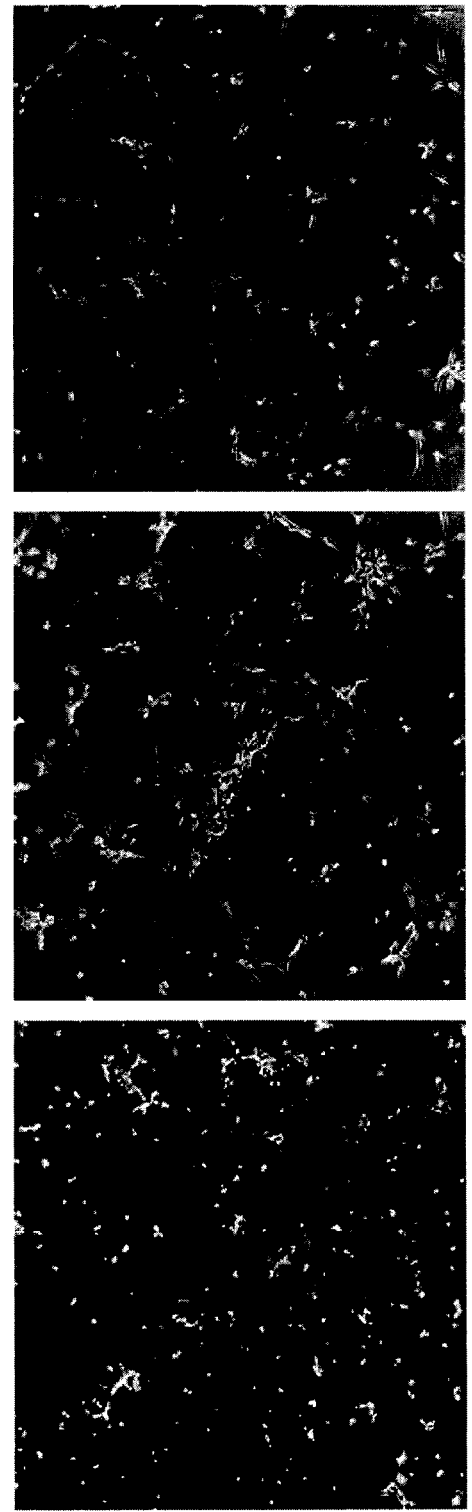
Figure 31:
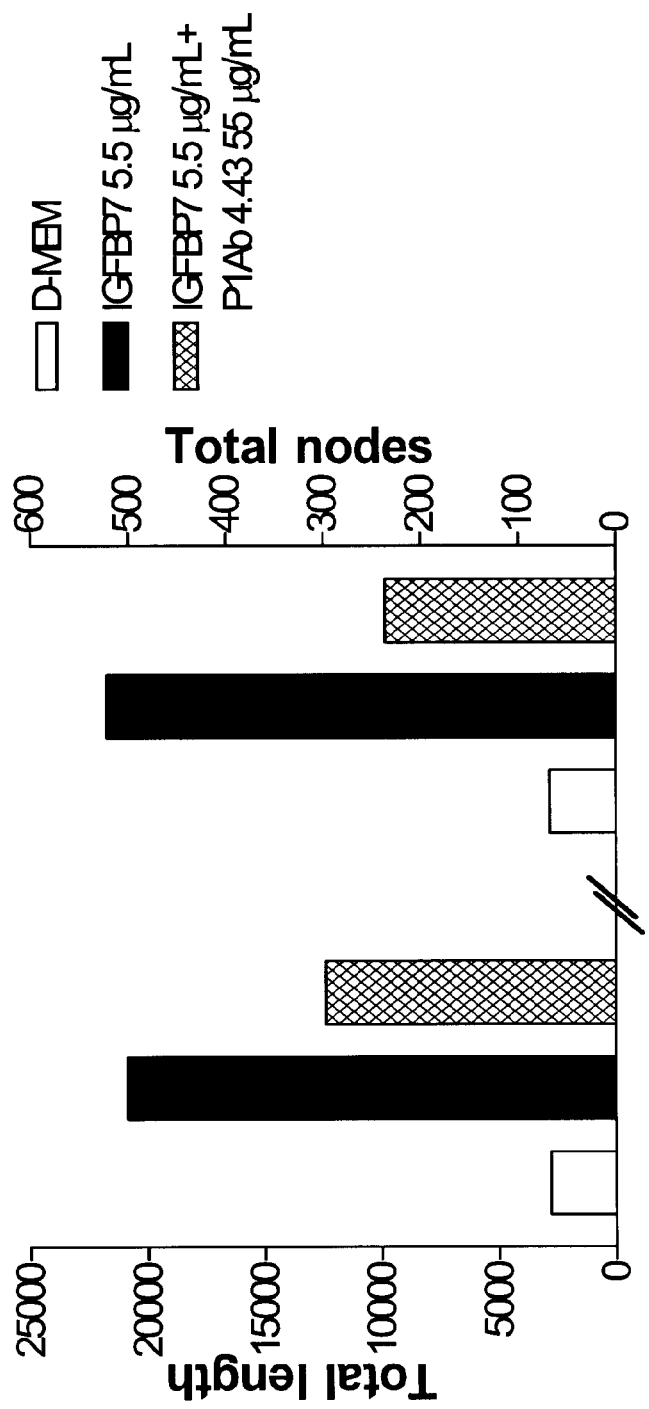
FIG. 31 shows the quantitation of the length of capillary-like tubes and the number of branching points after exposure of human brain endothelial cells grown in Matrigel to different treatments; demonstrations of inhibition of IGFBP7- and U87MG glioblastoma cell conditioned media-induced angiogenesis by pentameric 4.43 IGFBP7-Cy5.5.

In a set of experiments, and referring to FIGS. 21-22, the disclosed anti-IGFBP7 single domain antibodies were also shown to inhibit angiogenesis induced by IGFBP7; therefore, they have anti-angiogenic properties and could be used as a drug to inhibit pathological angiogenesis. Examples of diseases characterized by pathological angiogenesis are cancerous tumors, hemangiomas, diabetic retinal angiogenesis, etc The present invention provides diagnostic and/or therapeutic formulations that specifically recognize abnormal blood vessels in brain tumors. These formulations could be adapted for use in molecular imaging in vivo to diagnose brain tumor and evaluate the extent of angiogenesis and invasion and/or to prevent growth of abnormal tumor vessels, and/or to target/deliver other therapeutics to tumor vessels to destroy tumor vessels.

The diagnostic/therapeutic formulations described herein are based on single-domain antibodies that selectively bind to GBM tumor vessel biomarker, IGFBP7, and involve conjugates of anti-IGFBP7 single-domain antibodies with radiochemicals, optical contrast probes, and/or MRI contrast probes (for diagnostic imaging). They can also involve use of anti-IGFBP7 single domain antibody alone or its modifications for their application in histopathological or immunohistochemical diagnosis of abnormal tumor vessels in tumor biopsies and/or resections. Therapeutic applications include use of anti-IGFBP7 single domain antibody alone or its conjugate with therapeutic drug.

The present invention will be further illustrated in the following examples. However, it is to be understood that these examples are for illustrative purposes only and should not be used to limit the scope of the present invention in any manner.

EXAMPLE 1

Production of Recombinant IGFBP7

The full length IGFBP7 cDNA (GeneBank BC017201) in the vector pOTB7 was purchased from ATCC. Using the plasmid IGFBP7/pOTB7 as template, IGFBP7 cDNA fragment was amplified by PCR using forward primer 5'-TCGAATTCCCGCCATGGAGCGGCCGTCG-3' (SEQ ID NO:8) and reverse primer 5'-TAGGGATCCTAGCTCGGCACCTTCACCT-3' (SEQ ID NO:9). The PCR product was then digested with EcoR1 and BamH1 and inserted into a vector pTT5SH8Q2 (in frame with Streptag-II and polyhistidine epitopes) to yield IGFBP7/pTT5SH8Q2 plasmid and produced by transient transfection into human embryonic kidney 293 cell line stably expressing Epstein-Barr virus Nuclear Antigen-1 (EBNA1). Briefly, 500 mL of 293-EBNA1 cells (clone 6E; Y.D., unpublished) at a density of 1 million cells/mL were transfected with 475 µg of IGFBP7/pTT5SH8Q2 and 25 µg of GFP/pTT (pTT vector encoding the Green Fluorescent Protein) control plasmid using 1.5 mg of 25 kDa linear polyethylenimine (PEI) (ratio plasmid/PEI of 1:3). The culture was harvested 5 days after transfection, and the medium was clarified by centrifugation at 3500×g for 10 minutes and filtered through 0.22-µm membrane. Clarified culture medium was loaded on a cobalt-loaded Fractogel EMD chelate gravity flow column. The column was washed with 10 volumes of Wash Buffer (50 mM $NaH_2PO_4$, 300 mM NaCl and 25 mM imidazole, pH 7.0) and bound IGFBP7 was eluted by using Wash Buffer containing 300 mM imidazole. A buffer exchange for phosphate-buffered saline was performed by gel filtration on EconoPak columns (BioRad, Hercules, Calif., USA), and the final purified material was sterile-filtered, aliquoted, and stored at −80° C. Recombinant IGFBP7 was analyzed by SDS-PAGE (4-12% Bis-Tris NuPAGE gradient gel) and visualized by Coomassie blue staining. The activity of IGFBP7 was evaluated based on its ability to bind rh6Ckine/CCL21 chemokine.

EXAMPLE 2

Isolation of IGFBP7-specific sdAbs from a Llama Immune Phage Display Library

A male llama (*Lama glama*) was injected subcutaneously with 100, 75, 75, 50 and 50 µg IGFBP7 on days 1, 21, 36, 50 and 64, respectively. Complete Freund's Adjuvant (Sigma, St. Louis, Mo.) was used for the primary immunization and Incomplete Freund's Adjuvant was used for immunizations 2-4. Adjuvant was not used for the final immunization. The llama was bled one week following each immunization and heparinized blood was collected for immediate isolation of the peripheral blood leukocytes, which were stored at −80° C. until further use.

Total RNA was isolated from $2\times10^7$ leukocytes using a QIAamp RNA Blood Mini Kit (Qiagen). cDNA was synthesized using $pd(N)_6$ as primer and 566 ng total RNA as the template. Three different sense primers (called J' corresponding to the 5'-end of IgG) including MJ1 (GCCCAGCCGGC-CATGGCCSMKGTGCAGCTGGTGGAKTCTGGGGGA; SEQ ID NO:10), MJ2 (CAGCCGGCCATGGCCCAGG-TAAAGCTGGAGGAGTCTGGGGGA; SEQ ID NO:11) and MJ3 (GCCCAGCCGGCCATGGCCCAGGCTCAGG-TACAGCTGGTGGAGTCT; SEQ ID NO:12) and two antisense primers, corresponding to the $C_H2$ domain DNA sequence, $C_H2$ (CGCCATCAAGGTACCAGTTGA; SEQ ID NO:13) and $C_H2_b3$ (GGGGTACCTGTCATCCACGGAC-CAGCTGA (SEQ ID NO:14) were used to amplify the $V_H\text{-}C_H1\text{-Hinge-}C_H2$ region of conventional IgG or $V_H$H-Hinge-$C_H2$. Amplified products of approximately 600 bp from the primer combination J'-$C_H2$ were extracted from a 1% agarose gel and purified with a QIAquick Gel Extraction Kit (Qiagen) and the amplified products from primers J'-$C_H2_b3$ were PCR purified. In a second PCR reaction, the two primers of MJ7BACK (CATGTGTAGACTCGCGGC-CCAGCCGGCCATGGCC; SEQ ID NO:15) and MJ8FOR (CATGTGTAGATTCCTGGCCGGCCTGGC-CTGAGGAGACGGTGACCTGG; SEQ ID NO 16) were used to introduce SfiI restriction sites and to amplify the final sdAb fragments from the combined J'-$C_H2$ and J'-$C_H2_b3$ amplified products. The final PCR product was digested with SfiI and ligated into pMED1, a derivative of pHEN4, and transformed into E. coli TG1 (NEB, Ipswich, Mass.) by electroporation. Phage were rescued with helper phage M13KO7 (NEB).

The llama immune phage display library was panned against 1 mg/ml IGFBP7 that was preadsorbed to a Reacti-Bind™ maleic anhydride activated microtiter plate well. Approximately $10^{11}$ phages were added to the well and incubated at 37° C. for 2 hr for antigen binding. After disposal of unbound phages, the wells were washed six times with phosphate buffered saline supplemented with 0.05% Tween 20 (PBST) for round one and the washes were increased by one for each additional round. Phage were eluted by 10 min incubation with 100 µl 100 mM triethylamine and the eluate was subsequently neutralized with 200 µl 1M Tris-HCl (pH 7.5). Phage were amplified as described above but on a smaller scale. After four rounds of panning, eluted phage were used to infect exponentially growing E. coli TG1. Individual colonies were used in phage ELISA.

For phage ELISA, wells of a 96-well plate were coated overnight with 5 µg/ml IGFBP7 and then blocked with 1% casein for 2 hr at 37° C. Phage from individual clones were pre-blocked with 1% casein overnight, added to the pre-blocked wells and incubated for 1 hr. Phage ELISA was performed using the Detection Module Recombinant Phage Antibody System (GE Healthcare, Uppsala, Sweden), and positive phage clones were sequenced.

EXAMPLE 3

Expression of sdAbs and Pentabody

DNA encoding four representative clones were cloned into the BbsI and BamHI sites of a periplasmic expression vector pSJF2, which added a c-Myc detection tag and a 5×His purification tag at the C-terminus of the sdAbs. IGFBP7 4.43 was sub-cloned into the BspEI and BamHI sites of a pentamerization vector, pVT2, generating an expression vector for pentameric sdAb, or pentabody. IGFBP7 and pentameric IGFBP7 were expressed periplasmically and purified by IMAC. Briefly, clones were inoculated in 25 ml LB-Ampicillin (Amp) and incubated at 37° C. with 200 rpm shaking overnight. The next day, 20 ml of the culture was used to inoculate 1 l of M9 (0.2% glucose, 0.6% $Na_2HPO_4$, 0.3% $KH_2PO_4$, 0.1% $NH_4Cl$, 0.05% NaCl, 1 mM $MgCl_2$, 0.1 mM $CaCl_2$) supplemented with 0.4% casamino acids, 5 mg/l of vitamin B1 and 200 µg/ml of Amp, and cultured for 24 hr. 100 ml of 10×TB nutrients (12% Tryptone, 24% yeast extract and 4% glycerol), 2 ml of 100 mg/ml Amp and 1 ml of 1 M isopropyl-beta-D-Thiogalactopyranoside (IPTG) were added to the culture and incubation was continued for another 65-70 hr at 28° C. with 200 rpm shaking. E. coli cells were harvested by centrifugation and lysed with lysozyme. Cell lysates were centrifuged, and clear supernatant was loaded onto High-Trap™ chelating affinity columns (GE Healthcare) and His-tagged proteins were purified.

EXAMPLE 4

Surface Plasmon Resonance Analysis

Experiments were performed using a BIACORE 3000 optical sensor platform and research grade CM5 sensor chips (GE Healthcare). IGFBP7 sdAbs were immobilized on the sensor chip surface by standard amine coupling. All experiments were carried out in HEPES buffer [10 mM HEPES (pH 7.4), 150 mM NaCl, 3.4 mM EDTA, 0.005% Tween 20] at 25° C. Antibodies were injected at serial dilutions ranging from 0.4 nM to 1 µM at a flow rate of 30 µl/min unless otherwise indicated. The amount of bound analyte after subtraction from the blank control surface is shown as relative resonance units (RU). The double referenced sensorgrams from each injection series were analyzed for binding kinetics using BIAevaluation software (GE Healthcare). Dissociation constants ($K_D$) were calculated from the on- and off-rates ($k_{on}$ and $k_{off}$, respectively), as determined by global fitting of the experimental data to a 1:1 Langmuir binding model ($Chi^2<1$).

EXAMPLE 5

Orthotopic Brain Tumor Model

CD-1 nude mice (male, 6-8 weeks old) were purchased from Charles River Canada. The animals were housed in cages in groups of 3, maintained on a 12-h light/dark schedule with a temperature of 22° C. and a relative humidity of 50±5%. Food and water was available ad libitum. Brain tumors were generated in nude CD-1 mice by intracranial implantation of tumor-generating glioblastoma cell line, U87MG carrying deletion mutant of EGFR (ΔEGFR) cells. U87MG ΔEGFR cells were cultured in DMEM supplemented with 10% fetal calf serum and maintained in a humidified 5% $CO_2$ atmosphere at 37° C. Cells were harvested by trypsinization in EDTA/trypsin, washed in phosphate-buffered saline (PBS), and centrifuged at 200 g for 2 minutes three times. After cell density was determined, cells are brought into suspension at a final concentration of $5\times10^4$ cells/5 µl PBS. Cells were kept on ice until injection.

For intracerebral implantation of U87MG ΔEGFR cells, mice underwent isofluorane deep anesthesia and the scalp was swabbed with alcohol. The skin was incised and a 10 µl Hamilton syringe was used to inoculate 5 µl of cell suspension into the corpus striatum in the left hemisphere (3.0 mm deep; 1 mm anterior and 2.0 mm lateral to the bregma). All orthotopic U87MG ΔEGFR cell injection surgeries were approved by NRC-IBS Animal Care Committee. The U87MG ΔEGFR implanted tumors were allowed to grow for two weeks before beginning of the imaging experiments.

EXAMPLE 6

Labeling of sdAbs for Detection by In Vivo Imaging

Monomeric IGFBP7 (200 µg), monomeric NC11 (negative control) (200 µg) or pentameric IGFBP7sdAb (300 µg) was diluted in 10% sodium bicarbonate buffer pH 9.3 to achieve a solution pH of 8.0. To this mixture, 15 µg of near infrared Cy5.5 monoreactive NHS-ester in DMSO (GE Healthcare, Buckinghamshire, UK) was added and allowed to react during mixing at room temperature for four hours. After the incubation period, the antibody-cy5.5 conjugate was purified into PBS using a G-25 Sephadex column (Roche Applied Sciences, Laval, QC, Canada). Labeling time was optimized to achieve a dye/antibody ratio of one.

EXAMPLE 7

In Vivo Optical Imaging

Animals were subjected to in vivo imaging studies using a small-animal time-domain eXplore Optix pre-clinical imager (GE Healthcare, Milwakee, Wis.). At two weeks after intracranial implantation of U87MG ΔEGFR cells, Cy5.5-labeled single domain antibodies (1 nmol of IGFBP7sdAb, Pentameric-IGFBP7sdAb or NC11 negative control sdAb) were injected in animals via their tail vein, followed by imaging at multiple time points (pre-,10 min, 1 h, 2 h, 4 h, 20-24 h, 48 h, and 72 h) to determine antibody biodistribution. For the imaging experiments, mice were first anesthetized with isofluorane, and then positioned on an animal stage in a chamber which allows for maintenance of gaseous anesthesia and a chamber temperature of 36° C. At the end of in vivo imaging, mice were euthanized by intracardiac perfusion with heparinized saline while being deeply anesthetized with isofluorane. After perfusion the brains and organs were removed for ex vivo imaging and then frozen on dry ice and kept in at −80° C. until sectioning.

EXAMPLE 8

Tissue Preparation

Frozen human brain tumor tissue was obtained from the Foothills Hospital (Calgary, AB, Canada). Human and mouse brain tissues were embedded in Tissue-Tek freezing medium (Miles Laboratories, Elkhart, Ind.) and sectioned on a cryostat (Jung CM3000; Leica, Richmond Hill, ON, Canada) at 10 µm thickness, then mounted on Superfrost Plus microscope slides (Fisher Scientific, Nepean, ON, Canada). Slides were stored at −80° C. until immunohistochemical studies.

EXAMPLE 9

Immunohistochemisty—Human Tissue

Frozen human brain tumor tissue sections were thawed for a few seconds then incubated in methanol for 10 min at room temperature. Slides were rinsed with 0.2 M PBS (pH 7.3), followed by incubation with 0.1% Triton-X in PBS for 10 mins. Slides were then incubated with 5% donkey serum in PBS for 1 hour at room temperature. After blocking, slides were incubated with a polyclonal goat anti-human IGFBP7 antibody (1:30; R&D System, Minneapolis, Minn.) for 3 hours at room temperature. Sections were then washed three times with PBS, before incubation with secondary antibody, donkey anti-goat-Cy3 (1:500; Molecular Probes, Eugene, Oreg.) for 1 hour at room temperature. Slides were washed with PBS five times, before incubation with ULEX (1:20; Vector Laboratories) for 3 min at RT. Slides were then washed with PBS three times, dried of excess liquid and then coverslipped using DAKO fluorescent mounting media containing Hoechst (1:1,000; Dapi; Sigma, Oakville, ON, Canada). In control slides, the primary antibody was omitted. Coverslips were visualized under fluorescent microscope.

For single domain IGFBP7 antibody on human tissue, sections were blocked with 5% goat serum, and incubated with the pentavalent IGFBP7 sdAb (1:100 of a 1 mg/ml solution) for 3 h at r.t. These sections were then washed 3× in PBS, followed by incubation with rabbit polyclonal anti-veratoxin antibody (1:300, custom made in house) for 1 h. Sections were again washed 5×PBS and then incubated with secondary antibody, goat anti-rabbit alexa$^{647}$ (1:500; Molecular Probes, Eugene, Oreg.) for 1 h at r.t. Slides were washed with PBS five times, before incubation with ULEX (1:20; Vector Laboratories) for 3 min at RT. Slides were then washed with PBS three times, dried of excess liquid and then coverslips were mounted using DAKO fluorescent mounting media containing Hoechst (1:1,000; Dapi; Sigma, Oakville, ON, Canada). In control slides, the pentavalent single domain IGFBP7 antibody was omitted. Coverslips were allowed to harden at 4° C. overnight and then visualized under fluorescent microscope.

EXAMPLE 10

Immunohistochemistry—Mouse Tissue

Frozen mouse brain tumor tissue sections (from U87MFΔEGFR orthotopic brain tumors) were thawed for a few seconds then incubated in methanol for 10 min at room temperature. Slides were rinsed with 0.2 M PBS (pH 7.3), followed by incubation with 0.1% Triton-X in PBS for 10 mins. Slides were then incubated with 5% donkey serum in PBS for 1 hour at room temperature. After blocking, slides were incubated with a polyclonal goat anti-human IGFBP7 antibody (1:30; R&D System, Minneapolis, Minn.) for 3 hours at room temperature. Sections were then washed three times with PBS, before incubation with secondary antibody, FITC-labeled donkey anti-goat (1:500; Molecular Probes, Eugene, Oreg.) for 1 hour at room temperature. Slides were washed with PBS five times, before incubation with rat anti-mouse CD31 primary antibody for 1 hour at RT. Slides were then washed with PBS three times, before incubation with secondary antibody, goat-anti-rat alexa 568 (1:300) for 1 hour at room temperature. Slides were then washed with PBS five times, dried of excess liquid and then coverslips were mounted using DAKO fluorescent mounting media containing Hoechst (1:1,000; Dapi; Sigma, Oakville, ON, Canada). In control slides, the primary IGFBP7 antibody was omitted. Coverslips were allowed to harden at 4° C. overnight and then visualized under fluorescent microscope.

For single domain IGFBP7 antibody on mouse tissue, sections were blocked with 5% goat serum, and incubated with the pentavalent IGFBP7 sdAb (1:100 of a 1 mg/ml solution) for 3 h at r.t. These sections were then washed 3× in PBS, followed by incubation with rabbit polyclonal anti-veratoxin antibody (1:300, custom made in house) for 1 h. Sections were again washed 5×PBS and then incubated with secondary antibody, goat anti-rabbit alexa$^{647}$ (1:500; Molecular Probes, Eugene, Oreg.) for 1 h at r.t. Slides were washed with PBS five times, before incubation with ULEX (1:20; Vector Laboratories) for 3 min at RT. Slides were then washed with PBS three times, dried of excess liquid and then coverslips were mounted using DAKO fluorescent mounting media containing Hoechst (1:1,000; Dapi; Sigma, Oakville, ON, Canada). In control slides, the pentavalent single domain IGFBP7 antibody was omitted. Coverslips were allowed to harden at 4° C. overnight and then visualized under fluorescent microscope.

EXAMPLE 11

Ex Vivo Fluorescence Microscopy

For ex vivo fluorescent microscopy, animals injected with anti-IGFBP7 sdAb-cy5.5 for 24 hours were also injected via the tail vein with 40 μg of tomato lectin-FITC (Vector Laboraties, Burlingame, Calif.) in saline. Tomato lectin-FITC was allowed to circulate for 10 mins before animal was sacrificed and perfused with heparinized saline, their brain dissected and fixed in formalin overnight. Formalin fixed brains were cut using a vibratome (Ted Pella, Redding, Calif.) to create coronal 50 μm sections. Sections were washed with low molarity PBS, mounted on Superfrost Plus microscope slides (Fisher Scientific, Nepean, ON, Canada) and cover slipped in DAKO fluorescent mounting medium which contained Hoechst (1:1000). Sections were then visualized under an Olympus 1×81 inverted motorized microscope (Markham, Ontario, Canada).

EXAMPLE 12

Effects of sdAb Against IGFBP7 on Angiogenesis

Capillary-like tube (CLT) formation is an assay for measuring angiogenesis in vitro. Capillary-like tube (CLT) formation by human brain endothelial cells (HBEC) was determined using a growth factor reduced Matrigel™ (BD Bioscience, Beford, Mass., USA). 24-well tissue culture plate was coated with 300 μl of diluted Matrigel™ solution and incubated at 37° C. for at least an hour to allow the Matrigel™ solution to polymerize. HBEC (40,000 cells) were harvested in 500 μL D-MEM alone, D-MEM supplemented with 5.5 μg/ml of recombinant IGFBP7 in the absence or presence 55 μg/ml single-domain anti-IGFBP7 antibody (pentamer, P1 Ab), HBEC were then plated on top of the solidified Matrigel™ solution and maintained in an incubator at 37° C. overnight. Endothelial tube formation was observed 24 h later and digitally photographed under a phase contrast Olympus 1×50 microscope (Olympus U-CMT) at 20× magnification. Captured images were analyzed using Northern Eclipse v.5.0 software. Images were thresholded, converted to binary images, and skeletonized. The total length of the CLT networks and the number of nodes (branching points) formed by HBEC in the center of the well (80% of the total surface) were quantified.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

REFERENCES

1. Padlan, E. A. Anatomy of the antibody molecule. *Molecular immunology* 31, 169-217 (1994).
2. Hamers-Casterman, C. et al. Naturally occurring antibodies devoid of light chains. *Nature* 363, 446-448 (1993).
3. Nuttall, S. D. et al. Isolation and characterization of an IgNAR variable domain specific for the human mitochondrial translocase receptor Tom70. *European journal of biochemistry/FEBS* 270, 3543-3554 (2003).
4. Jespers, L., Schon, O., Famm, K. & Winter, G. Aggregation-resistant domain antibodies selected on phage by heat denaturation. *Nat Biotechnol* 22, 1161-1165 (2004).
5. To, R. et al. Isolation of monomeric human V(H)s by a phage selection. *J Biol Chem* 280, 41395-41403 (2005).
6. Zhang, J. et al. A pentavalent single-domain antibody approach to tumor antigen discovery and the development of novel proteomics reagents. *J Mol Biol* 341, 161-169 (2004).
7. Zhang, J. et al. Pentamerization of single-domain antibodies from phage libraries: a novel strategy for the rapid generation of high-avidity antibody reagents. *J Mol Biol* 335, 49-56 (2004).
8. Nielsen, U. B., Adams, G. P., Weiner, L. M. & Marks, J. D. Targeting of bivalent anti-ErbB2 diabody antibody fragments to tumor cells is independent of the intrinsic antibody affinity. *Cancer research* 60, 6434-6440 (2000).
9. de Kruif, J. & Logtenberg, T. Leucine zipper dimerized bivalent and bispecific scFv antibodies from a semi-synthetic antibody phage display library. *J Biol Chem* 271, 7630-7634 (1996).
10. Ridgway, J. B., Presta, L. G. & Carter, P. 'Knobs-into-holes' engineering of antibody CH3 domains for heavy chain heterodimerization. *Protein Eng* 9, 617-621 (1996).

The invention claimed is:

1. An isolated or purified antibody or fragment thereof, comprising:
   a sequence of complementarity determining region (CDR) 1 selected from sequences comprising RTFSRLAM (SEQ ID NO:3) and RTSRRYAM (SEQ ID NO:6);
   a sequence of CDR2 comprising GISRSGDGTHYAYSV (SEQ ID NO:4); and
   a sequence of CDR3 comprising AARTAFYYYGNDYNY (SEQ ID NO:5), and
   wherein the antibody or fragment thereof binds to Insulin-like Growth Factor Binding Protein 7 (IGFBP7).

2. The isolated or purified antibody or the fragment thereof of claim 1, wherein the antibody or fragment thereof is a single-domain antibody (sdAb).

3. The isolated or purified antibody or the fragment thereof of claim 2, wherein the sdAb is of camelid origin.

4. The isolated or purified antibody or the fragment thereof of claim 1, comprising the sequence:
AIAIAVALAGFATVAQAQVKLEESGGGS-VQPGGSLRLSCAASGRTFSRLAMGWFRQAP GKERELVAGISRSGDGTHYAYSVKGRFT-ISRDNAANTVELQMNSLKPEDTAVYFCAAA RTAFYYYGNDYNYWGQGTQVTVSS (SEQ ID NO:1), or a sequence at least 95% identical thereto.

5. The isolated or purified antibody or the fragment thereof of claim 4, conjugated to a member of the group consisting of cytotoxic agents, and cytostatic drugs.

6. The isolated or purified antibody or the fragment thereof of claim 1, comprising the sequence:
AIAIAVALAGFATVA-QAQVKLEESGGGLVQAGGSLRLSCAAS-GRTSRRYAMGWFRQAP GKEREFVAGISRS-GDGTHYAYSVKGRFTISRDNAANTVELQMNSLK PEDTAVYFCAAA RTAFYYYGNDYNY-WGQGTQVTVSS (SEQ ID NO. 2), or a sequence at least 95% identical thereto.

7. The isolated or purified antibody or the fragment thereof of claim 1, wherein the antibody or fragment thereof is multivalent.

8. The isolated or purified antibody or fragment thereof of claim 1, further comprising a detectable marker.

9. The isolated or purified antibody or the fragment thereof of claim 8, wherein said detectable marker is selected from the group consisting of radioisotopes, fluorochromes, dyes, enzymes and biotin.

10. The isolated or purified antibody or the fragment thereof of claim 1, wherein the antibody or fragment thereof is humanized.

11. A method for detecting IGFBP7 in a biological sample, comprising the steps of:
    a) exposing a sample suspected of containing IGFBP7 to a detectably labelled anti-IGFBP7 antibody or fragment thereof of claim 1;
    b) washing the sample; and
    c) detecting the presence of said detectably labelled anti-IGFBP7 antibody or fragment in said sample.

12. The method according to claim 11, wherein the biological sample is blood cells, tissue cells, or a solid tissue specimen.

13. A composition comprising the antibody or fragment thereof of claim 1 and a pharmaceutically acceptable excipient or carrier.

14. The method according to claim 12, wherein the sample of tissue cells or the solid tissue specimen is selected from the group consisting of brain, lung, colon, pancreas, stomach, and breast tissue.

15. A method for diagnosing a neoplastic disease or a tumor angiogenesis disease, comprising the steps of:
    a) obtaining a tissue sample from a patient suspected of having said disease;
    b) exposing said tissue sample to a detachably labelled anti-IGFBP7 antibody or fragment thereof of claim 1;
    c) washing said tissue sample; and
    d) detecting the presence of said detectably labelled anti-IGFBP7 antibody or fragment thereof in said tissue sample.

16. The method according to claim 15, wherein the disease is brain cancer.

17. The method according to claim 15, wherein the disease is selected from the group consisting of Grade I, II, III, and IV brain gliomas.

18. A method for imaging neovascularization in an organism, comprising the steps of:
    a) administering to said organism a detectably labelled anti-IGFBP7 antibody or fragment thereof of claim 1 into circulation; and
    b) detecting an amount of said detectably labelled anti-IGFBP7 antibody or fragment thereof which binds to said site.

19. The method of claim 18, wherein the step of detecting is a method selected from the group consisting of: x-ray imaging, computed tomography (CT), optical imaging, computed tomography angiography (CTA), electron beam tomography (EBT), magnetic resonance imaging (MRI), magnetic resonance angiography (MRA), positron emission tomography (PET), and single-photon emission computed tomagraph (SPECT).

20. An in vivo method for predicting brain tumor growth by detecting or evaluating neovascularization in the brain tumor of a subject comprising:
    a) administering to the subject an effective amount of the anti-IGFB7 antibody or fragment thereof of claim 1, wherein the anti-IGFB7 antibody or fragment thereof further comprises a contrast agent;
    b) detecting said contrast agent, thereby forming an image of said accumulated anti-IGFBP7 antibody or fragment thereof in the brain tumor; and
    c) predicting risk of brain tumor growth in the subject based on the image formed.

21. The method of claim 20, wherein the step of predicting is made based on a quantitative measure of the accumulation of the contrast agent in the brain tumor of the subject.

* * * * *